United States Patent
Voronov et al.

(10) Patent No.: US 9,442,091 B2
(45) Date of Patent: Sep. 13, 2016

(54) REDUCED ARTIFACT DENATURING CAPILLARY ELECTROPHORESIS OF NUCLEIC ACIDS

(75) Inventors: Sergey V. Voronov, Sharon, MA (US); Jork Nolling, Hopedale, MA (US)

(73) Assignee: QIAGEN MANSFIELD, INC., Mansfield, MA (US)

(*) Notice: Subject to any disclaimer, the term of this patent is extended or adjusted under 35 U.S.C. 154(b) by 666 days.

(21) Appl. No.: 13/982,509

(22) PCT Filed: Jan. 30, 2012

(86) PCT No.: PCT/US2012/023114
§ 371 (c)(1),
(2), (4) Date: Oct. 7, 2013

(87) PCT Pub. No.: WO2012/106244
PCT Pub. Date: Aug. 9, 2012

(65) Prior Publication Data
US 2014/0021050 A1    Jan. 23, 2014

Related U.S. Application Data

(60) Provisional application No. 61/438,070, filed on Jan. 31, 2011.

(51) Int. Cl.
*G01N 27/447* (2006.01)
*G01N 27/453* (2006.01)
*C12Q 1/68* (2006.01)

(52) U.S. Cl.
CPC ......... *G01N 27/44743* (2013.01); *C12Q 1/686* (2013.01)

(58) Field of Classification Search
CPC ................ G01N 27/44708; G01N 27/44743; G01N 27/44791; C12N 15/101
See application file for complete search history.

(56) References Cited

U.S. PATENT DOCUMENTS 6,475,362 B1 * 11/2002 Gorfinkel ......... G01N 27/44743
  204/451
7,056,426 B2    6/2006 Panattoni
(Continued)

FOREIGN PATENT DOCUMENTS

EP    0773225    5/1997

OTHER PUBLICATIONS

Lagally et al., Lab on a Chip, 1(2):102-107 (2001). "Fully integrated PCR-capillary electrophoresis microsystem for DNA analysis."
Drossman et al, Anal. Chem., 62: 900-903 (1990).
(Continued)

*Primary Examiner* — Alexander Noguerola
(74) *Attorney, Agent, or Firm* — Nixon Peabody LLP; Mark J. FitzGerald

(57) ABSTRACT

Described are methods of reducing the incidence and/or magnitude of artifacts in denaturing nucleic acid capillary electrophoresis (CE). Methods and systems described serve to dismiss non-denatured DNA from the tip of the capillary after sample injection and prior to electrophoretic separation of loaded nucleic acids. Among the methods disclosed are the application of a brief reverse-polarity pulse to the capillary prior to separation but after removal of the capillary from the sample reservoir, and transiently heating the capillary to cause expansion of the separation matrix after removal of the capillary from the sample reservoir.

20 Claims, 18 Drawing Sheets

(56) References Cited

U.S. PATENT DOCUMENTS

2002/0100690 A1 8/2002 Herbert
2002/0144906 A1* 10/2002 Naughton ........ G01N 27/44704
204/451

OTHER PUBLICATIONS

Huang et al, Anal. Chem., 64: 2149-2154 (1992).
Swerdlow et al, Nucleic Acids Research, 18: 1415-1419 (1990).
Williams, Methods 4: 227-232 (1992).

* cited by examiner

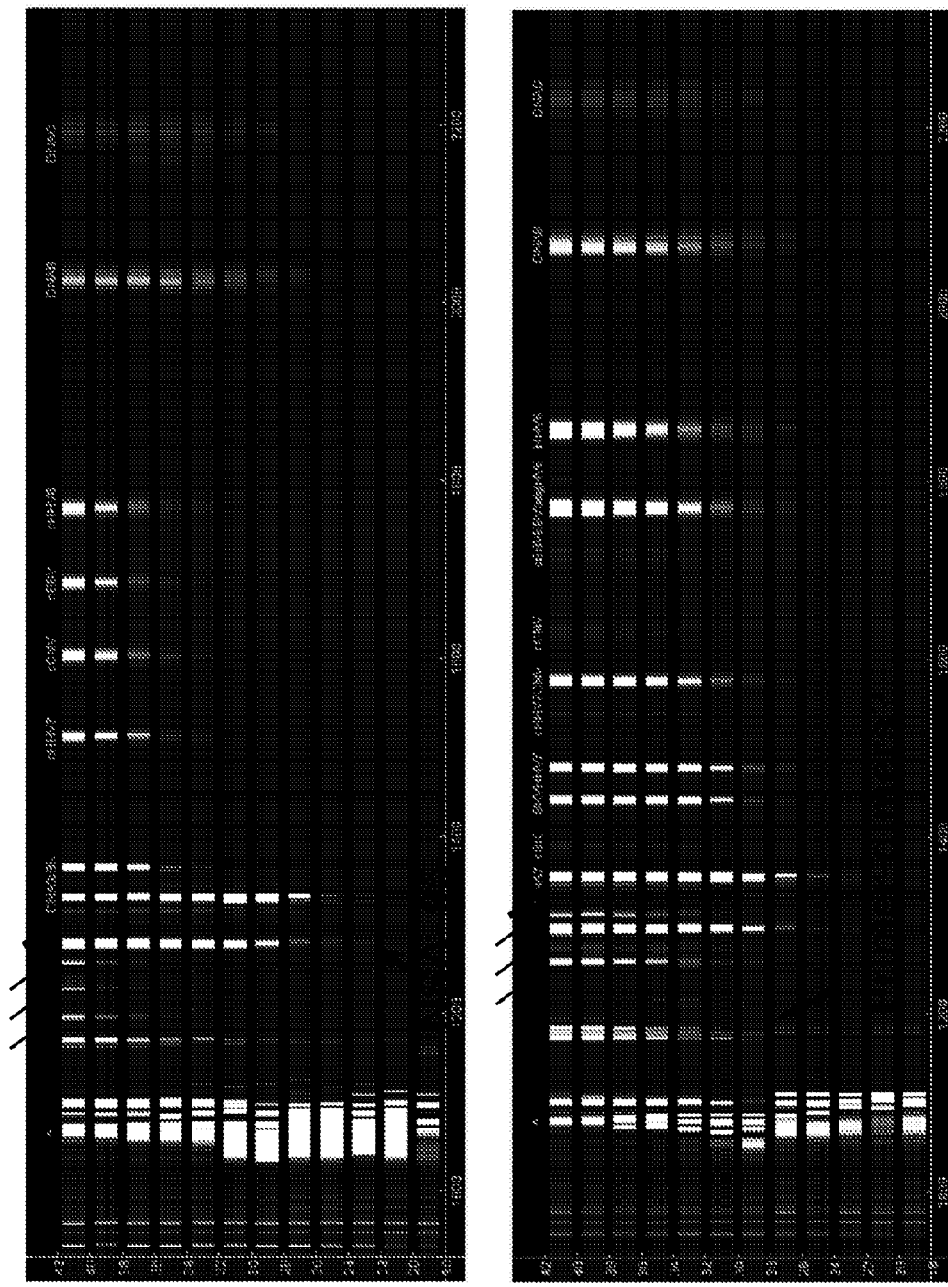
Figure 1. ViraQuant ICE 1.1: Shadows

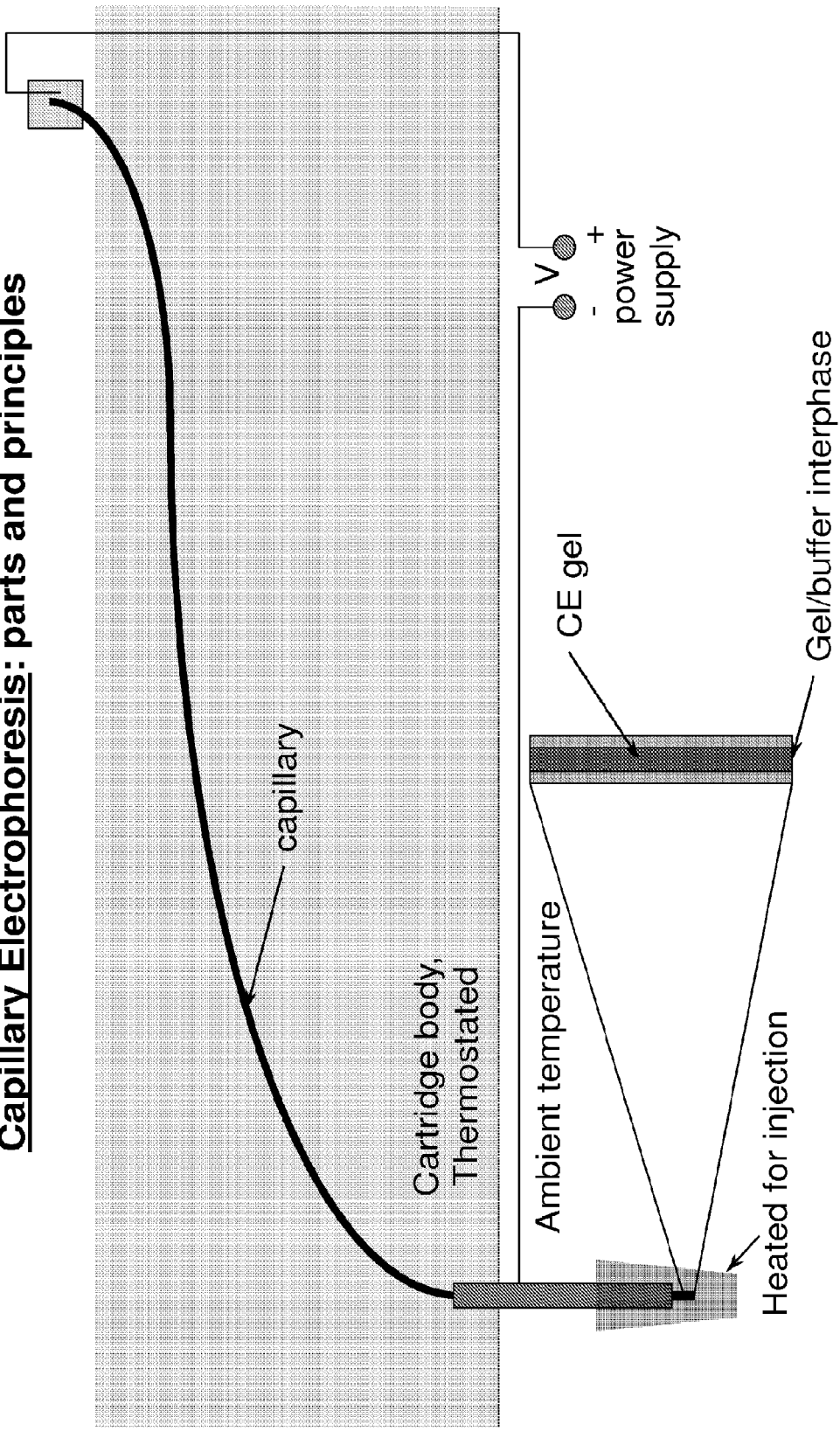

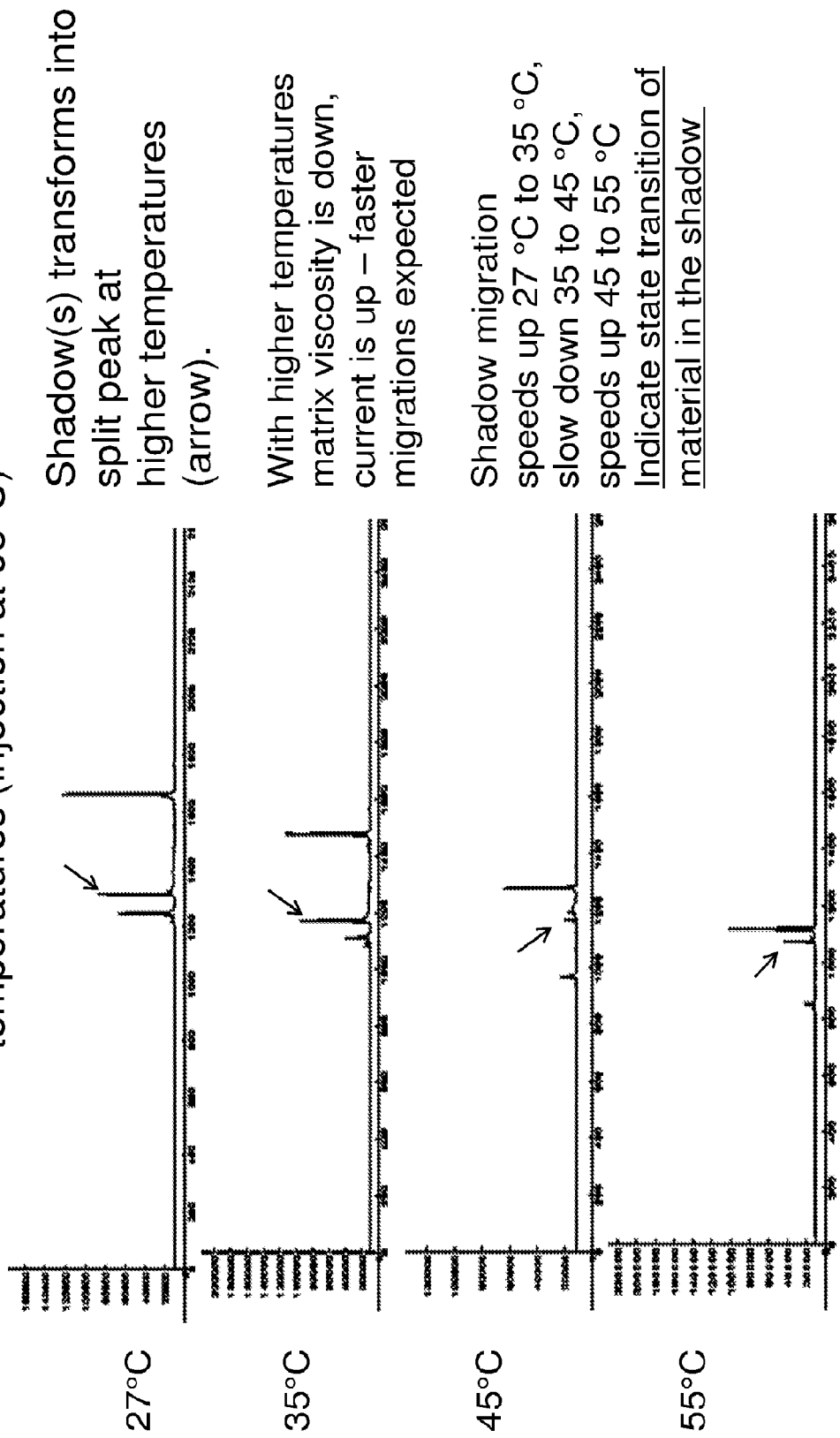

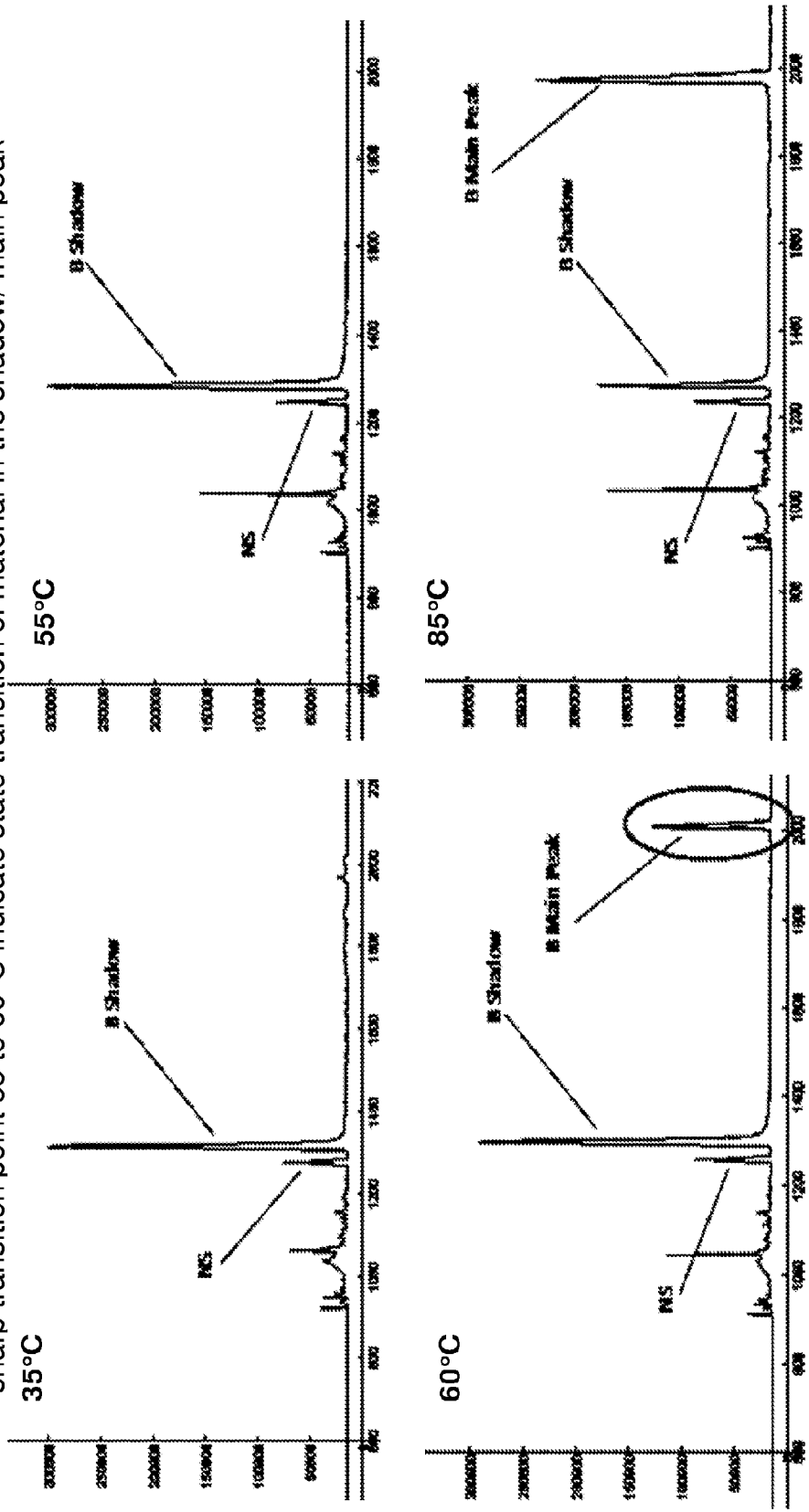

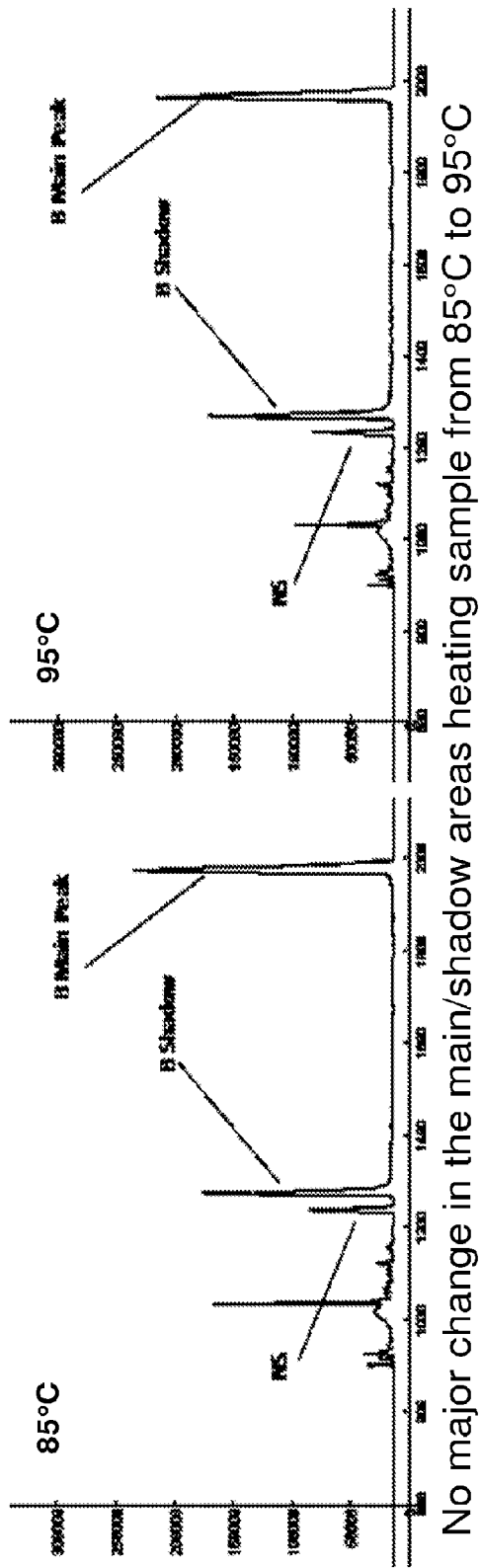

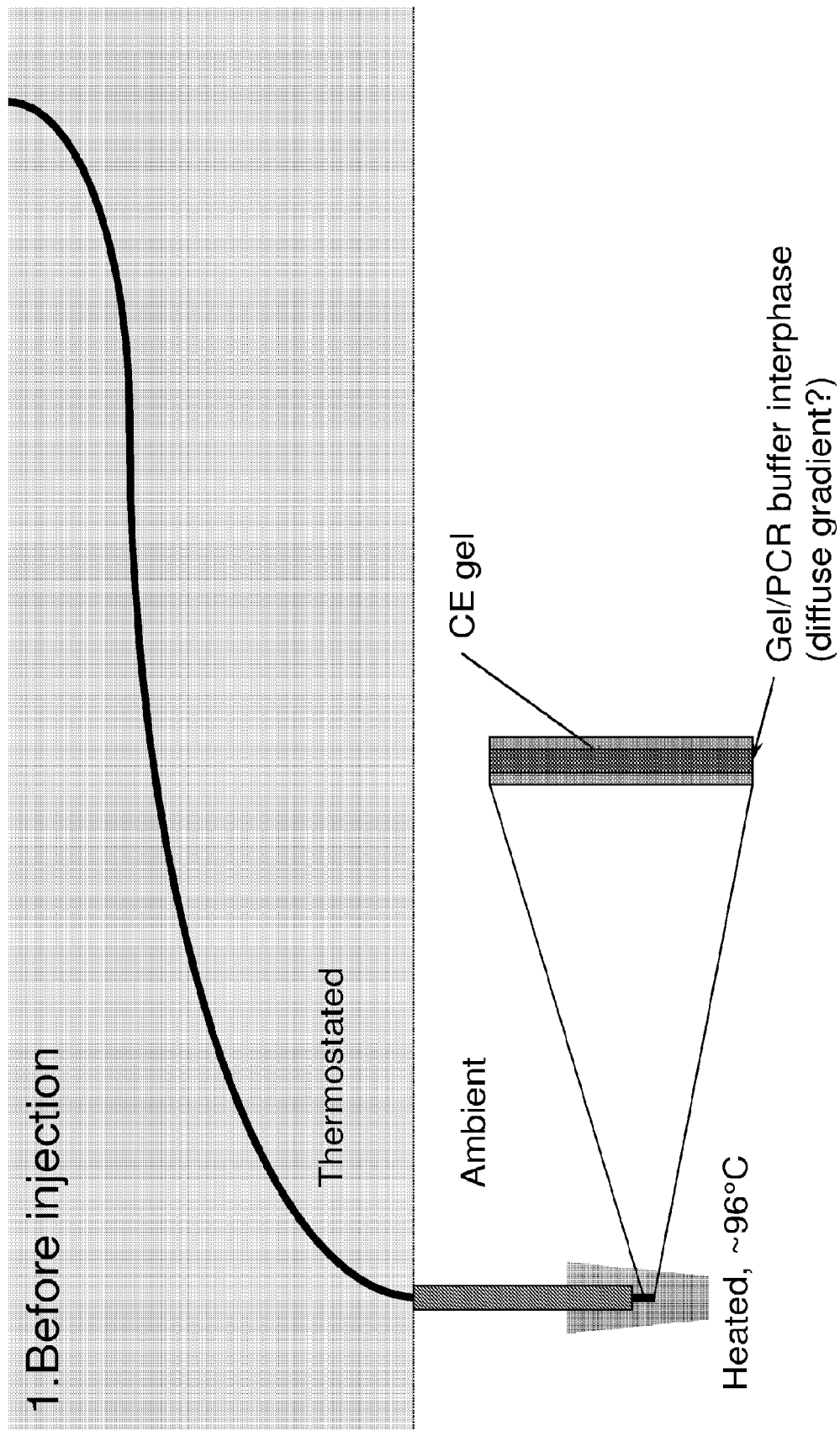
Figure 6A. Injection-related events in the capillary and at the tip

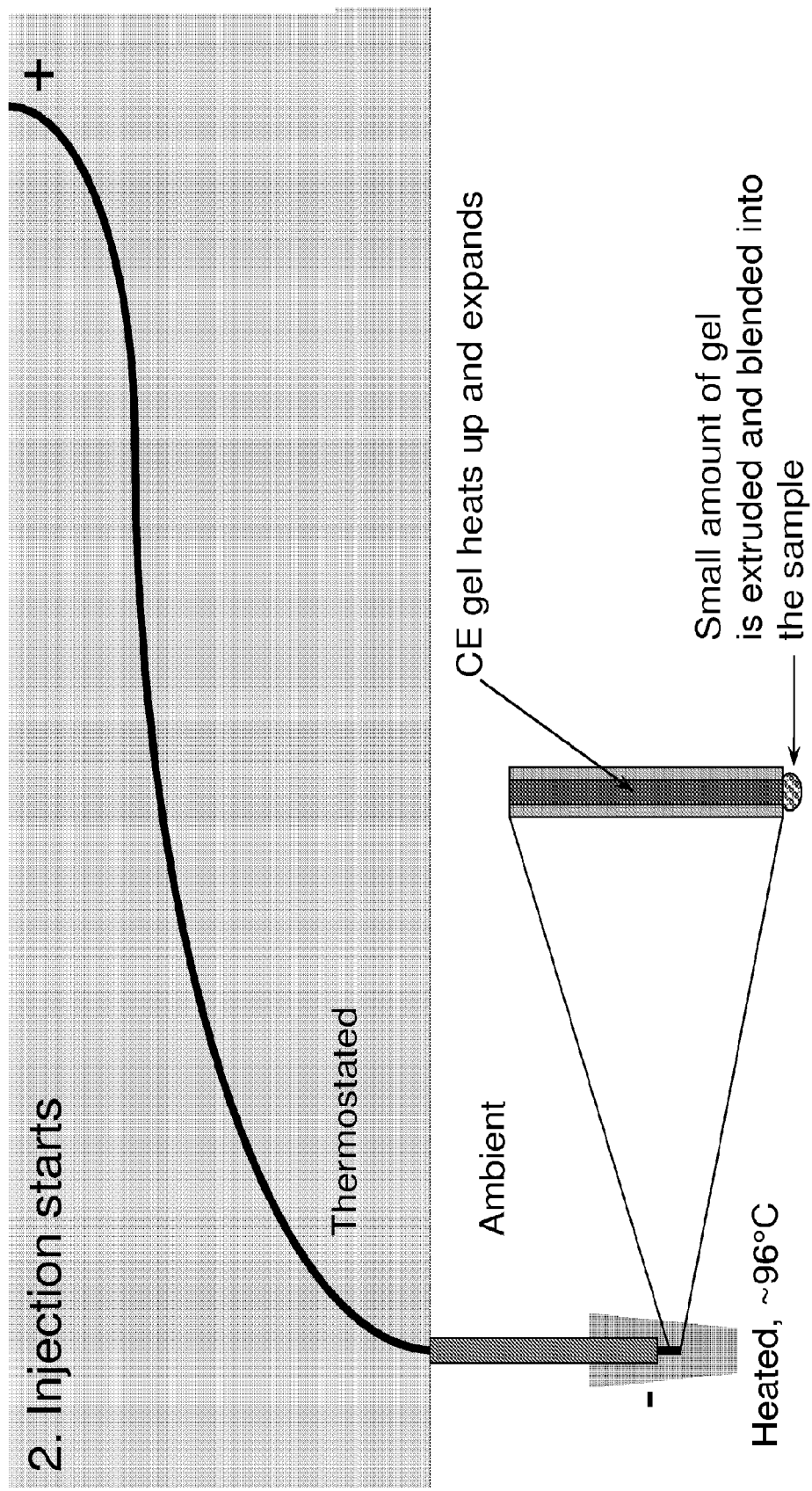
Figure 6B. Injection-related events in the capillary and at the tip

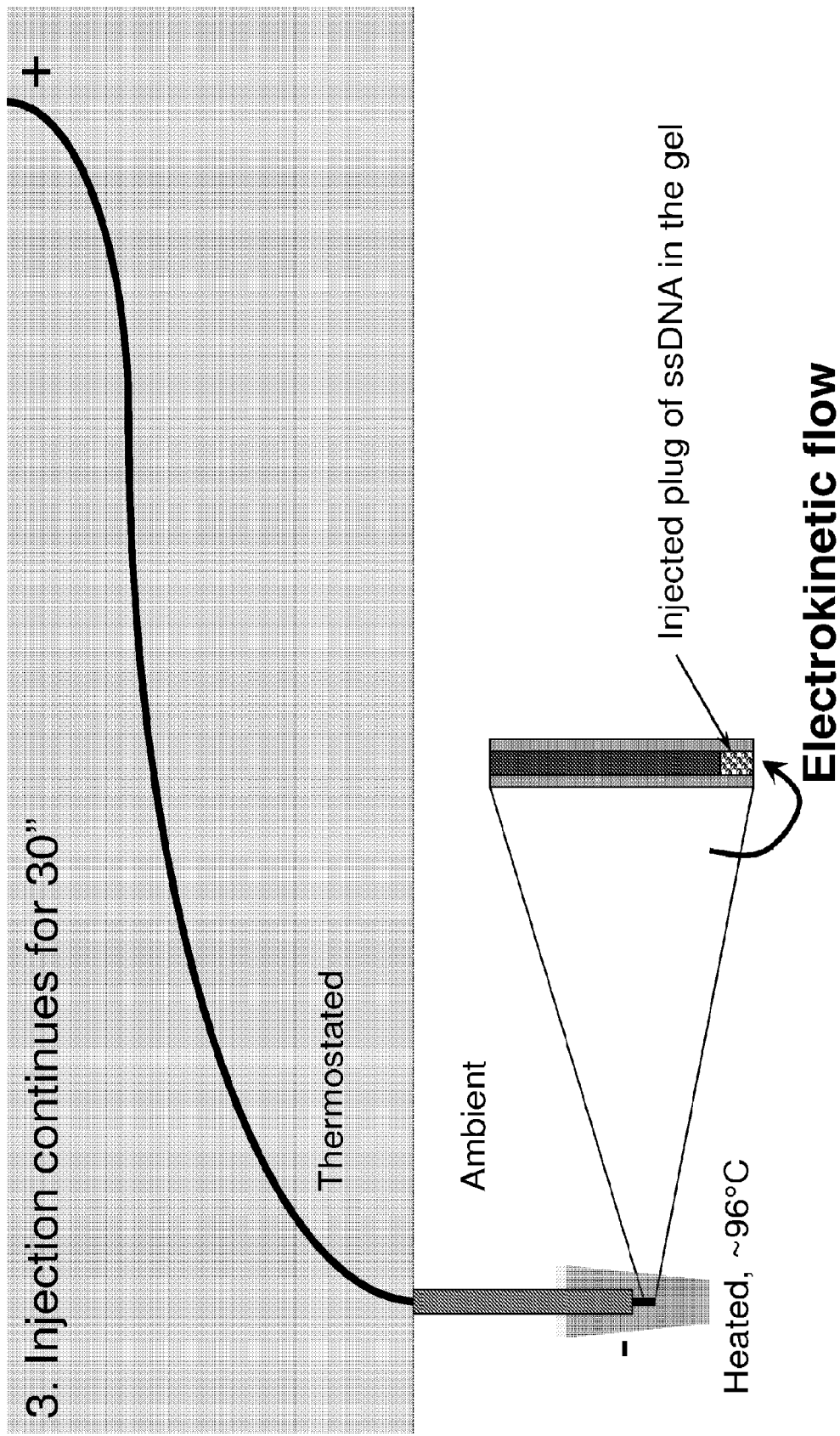
Figure 6C. Injection-related events in the capillary and at the tip

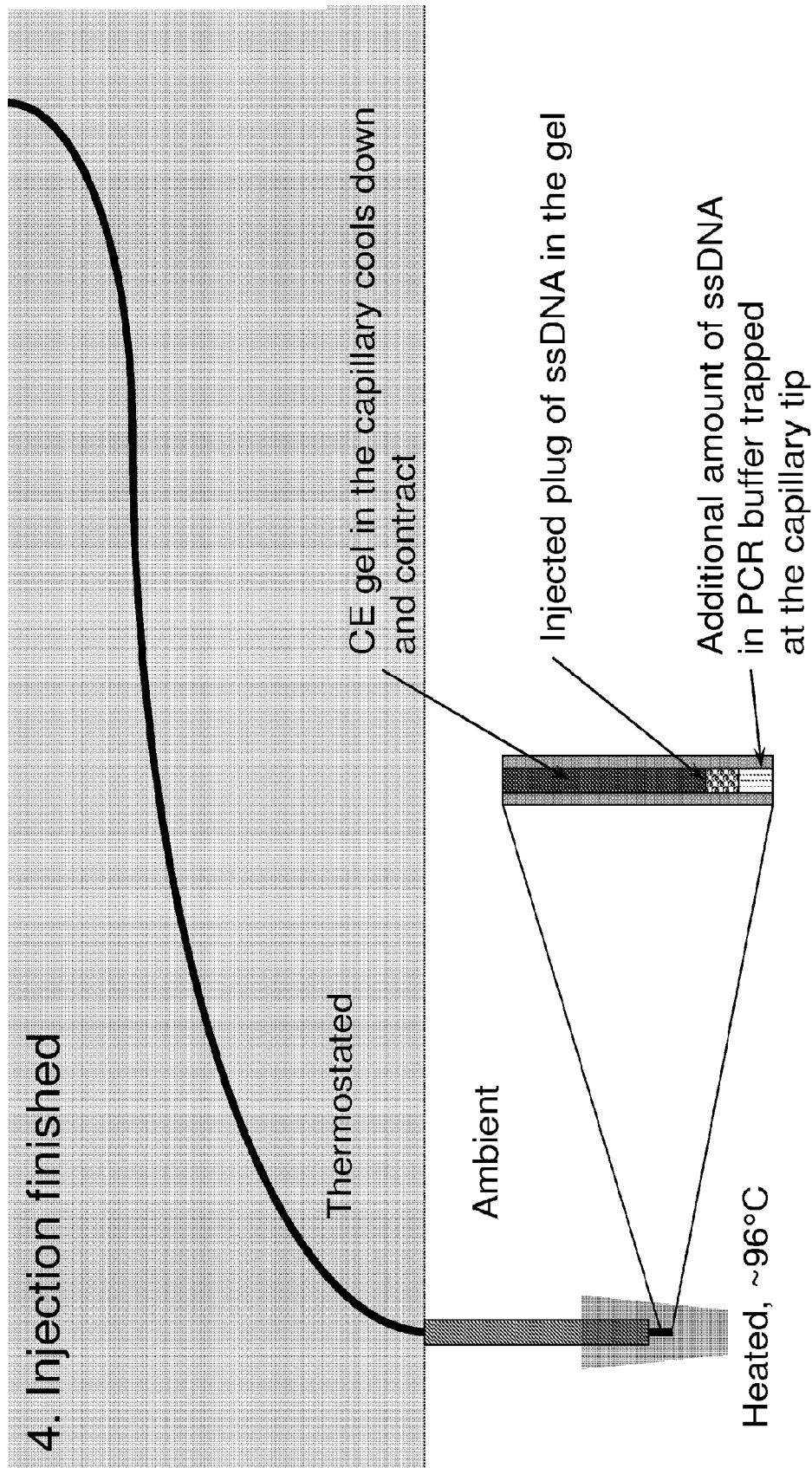
Figure 6D. Injection-related events in the capillary and at the tip

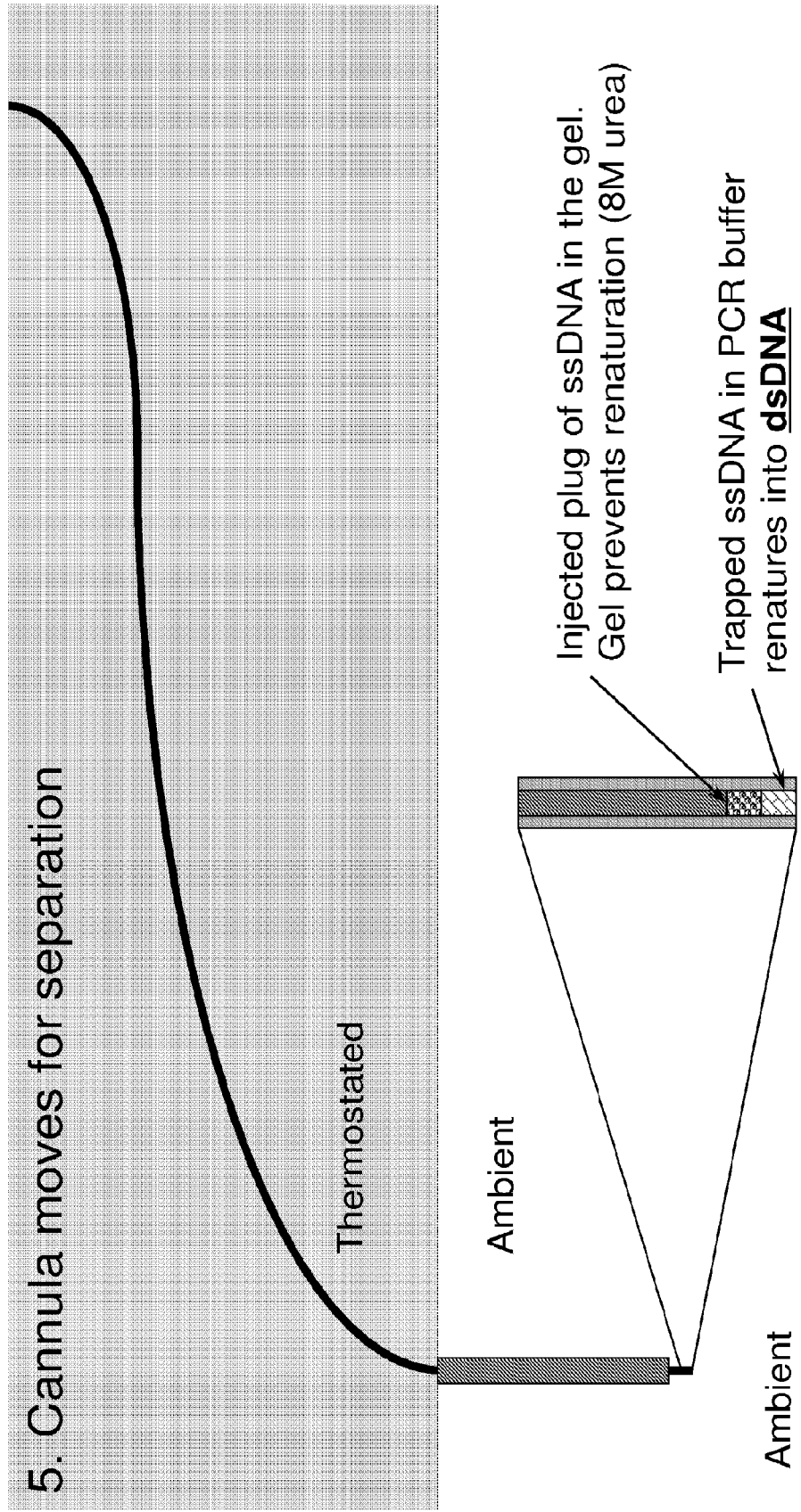
Figure 6E. Injection-related events in the capillary and at the tip

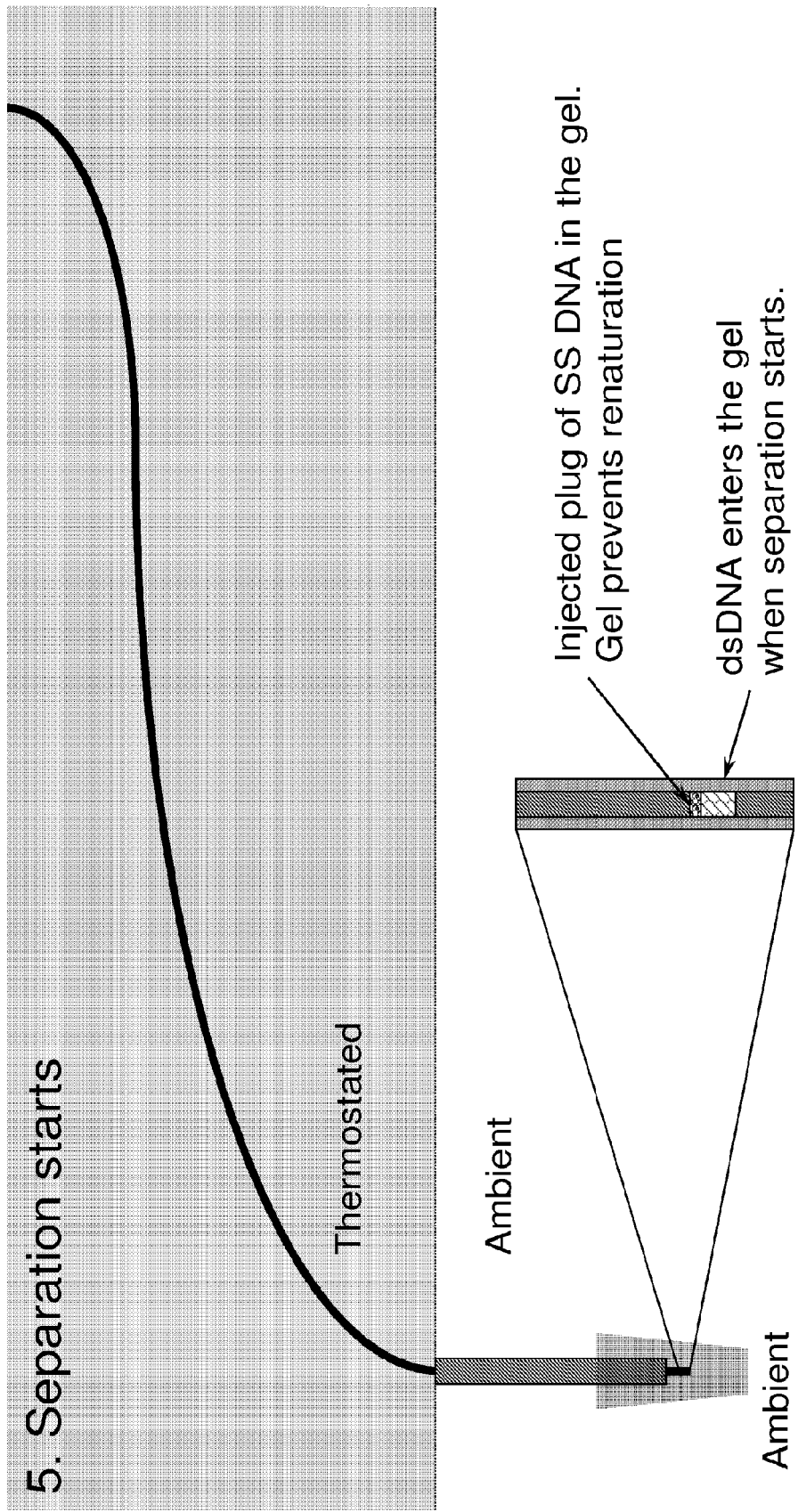
Figure 6F. Injection-related events in the capillary and at the tip

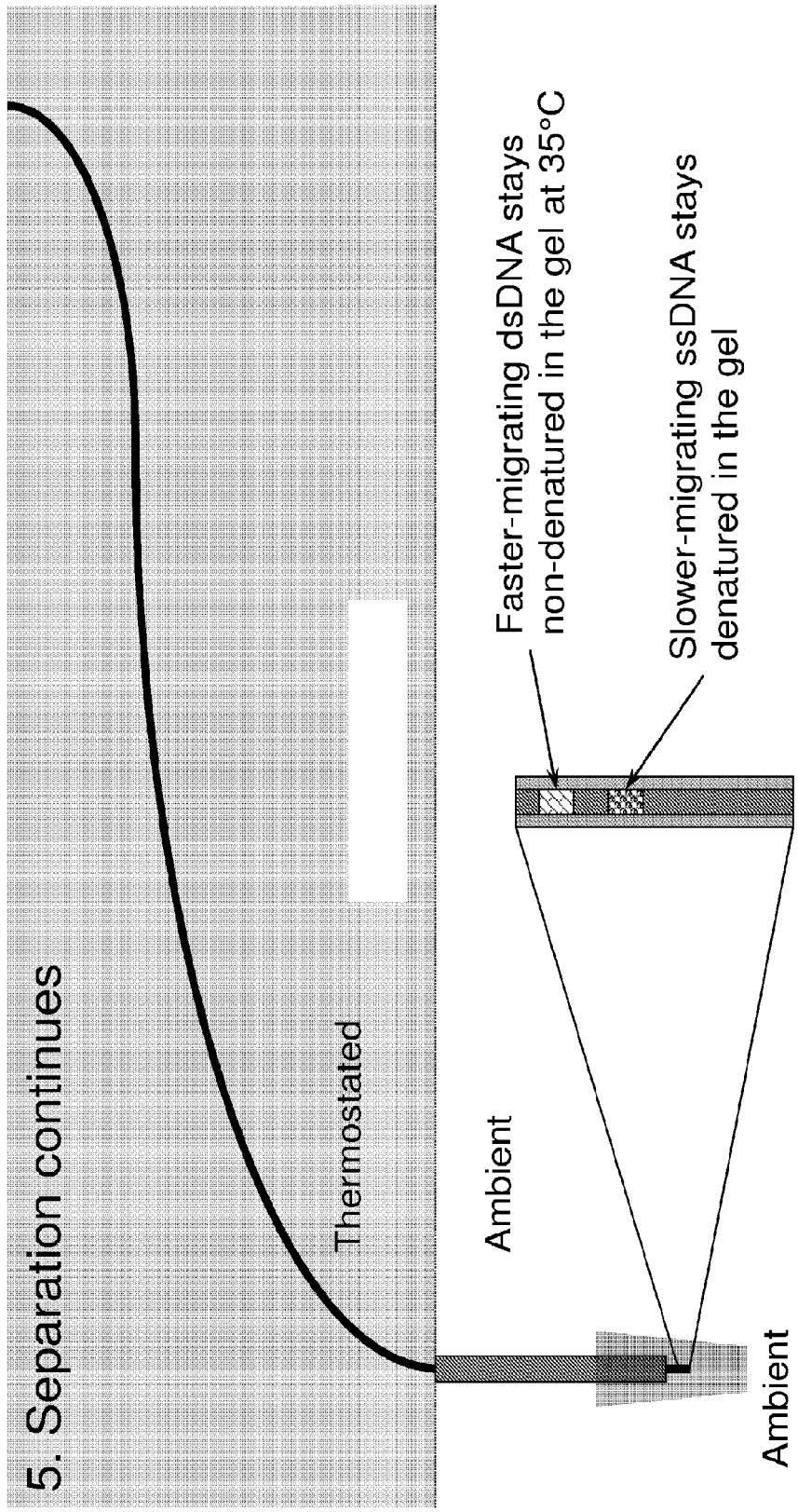
Figure 6G. Injection-related events in the capillary and at the tip

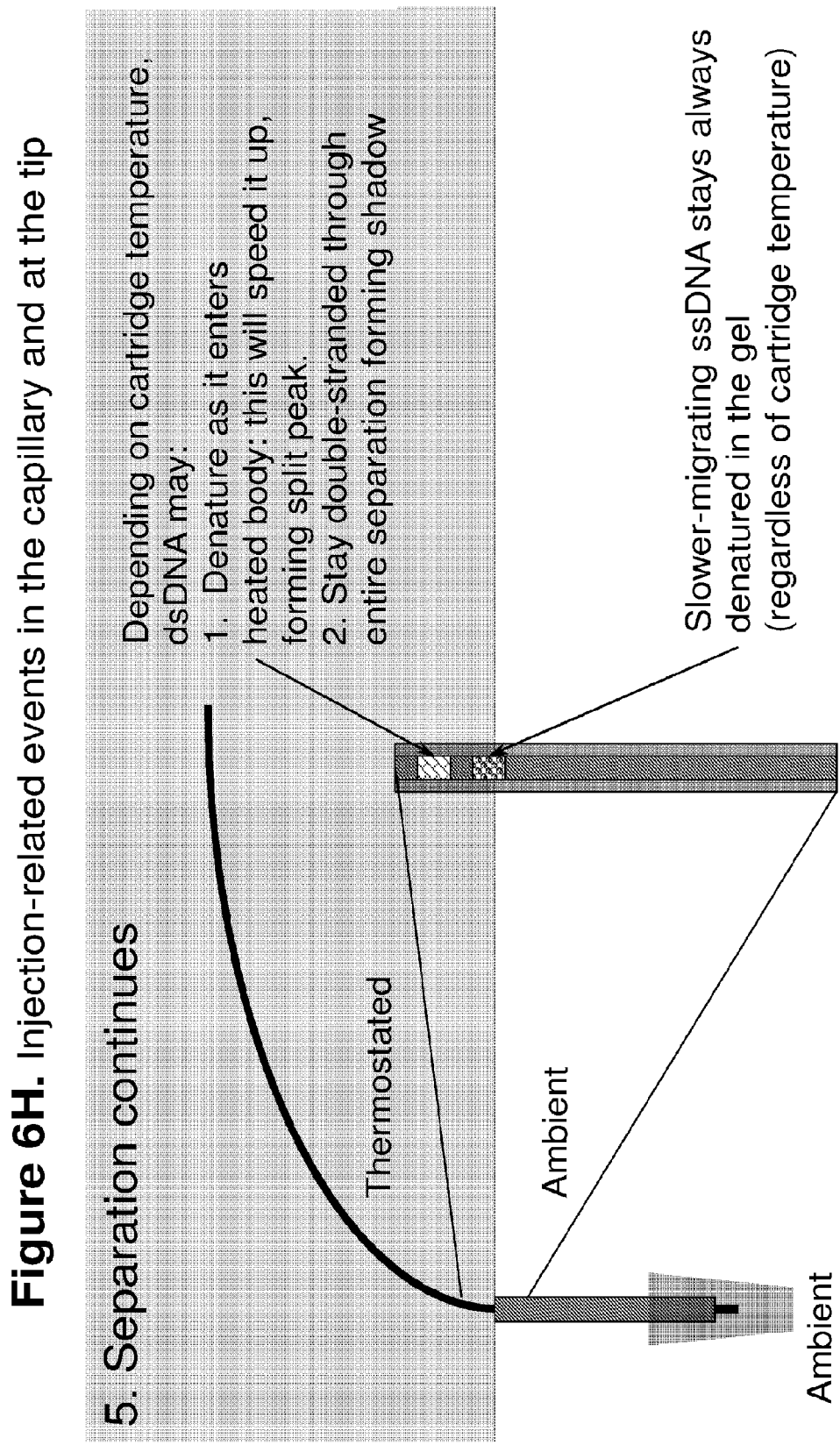
Figure 6H. Injection-related events in the capillary and at the tip

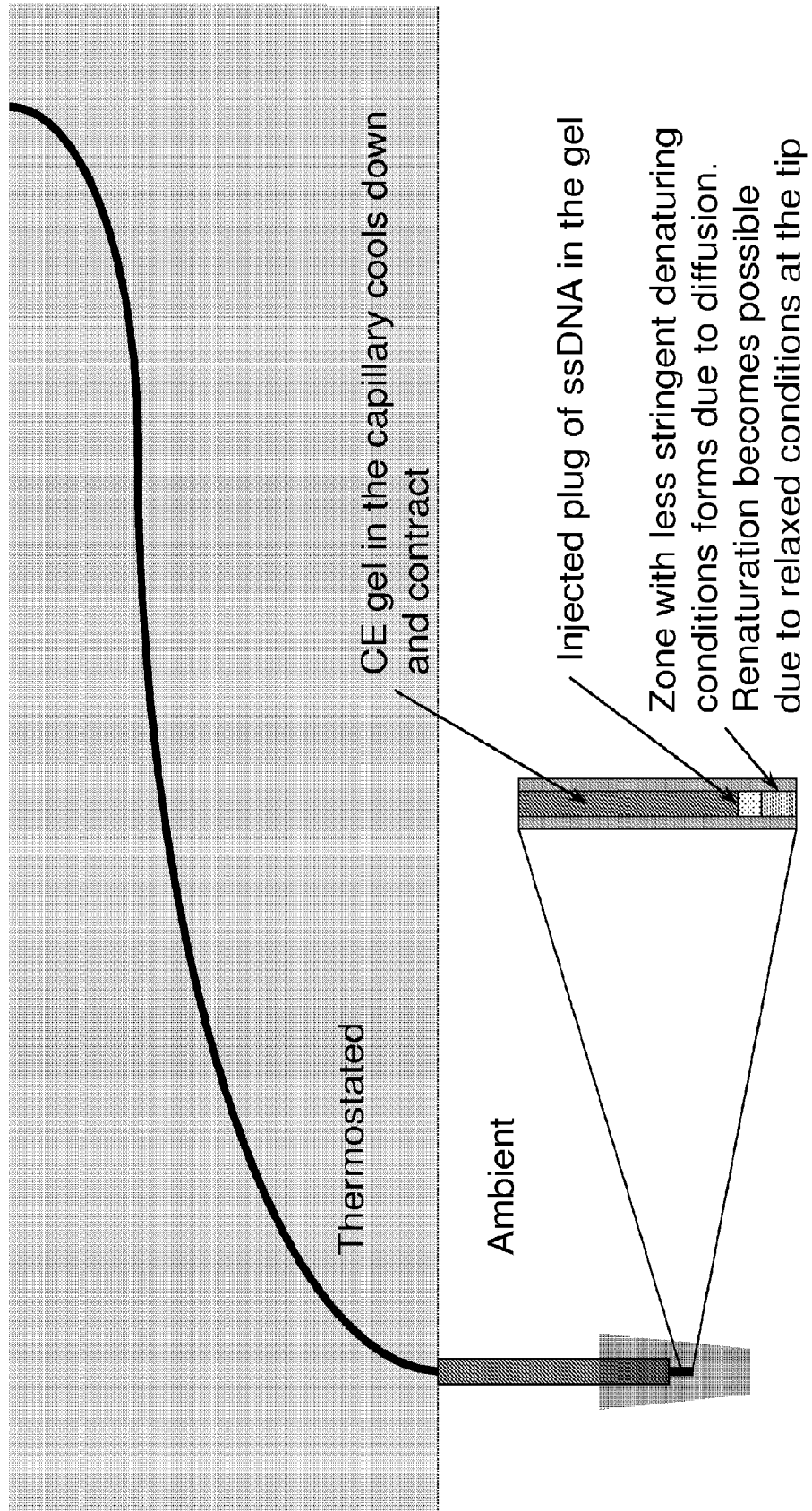
Figure 7. Alternative option
*(combination with original also possible)*

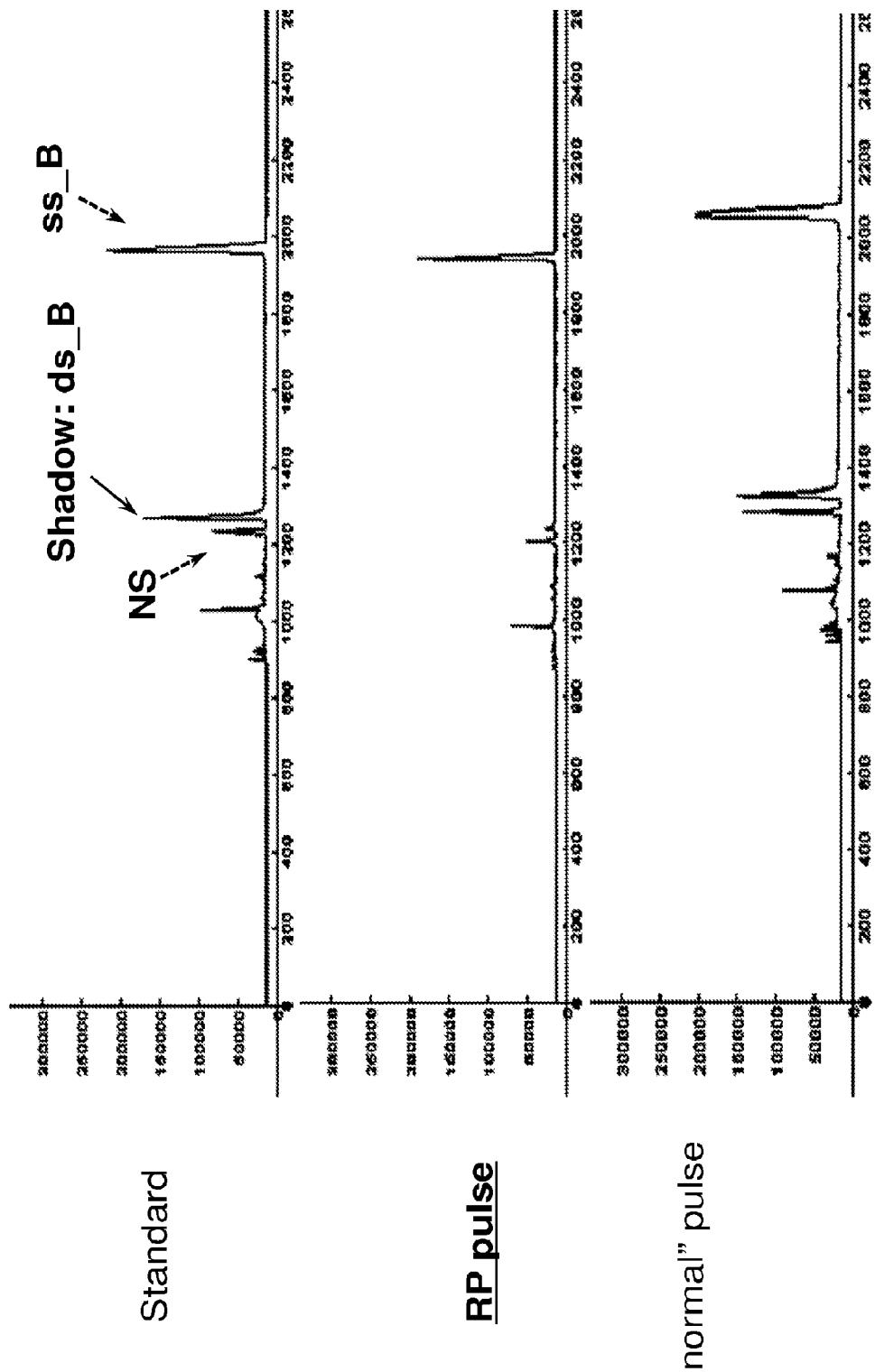

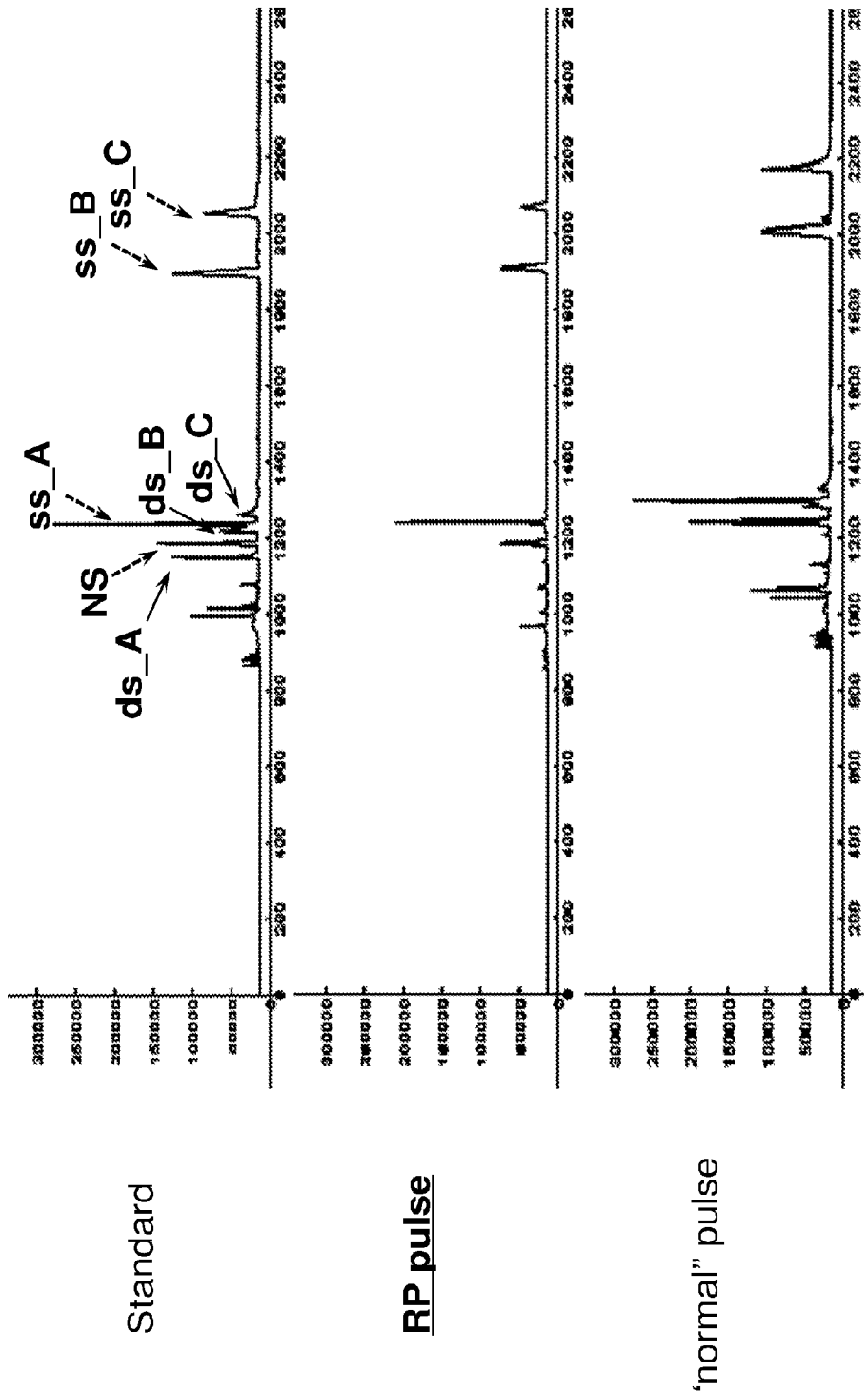
Figure 8B. Result: 3 ampicons

Figure 8C. Result: VQ-NTC (G02)

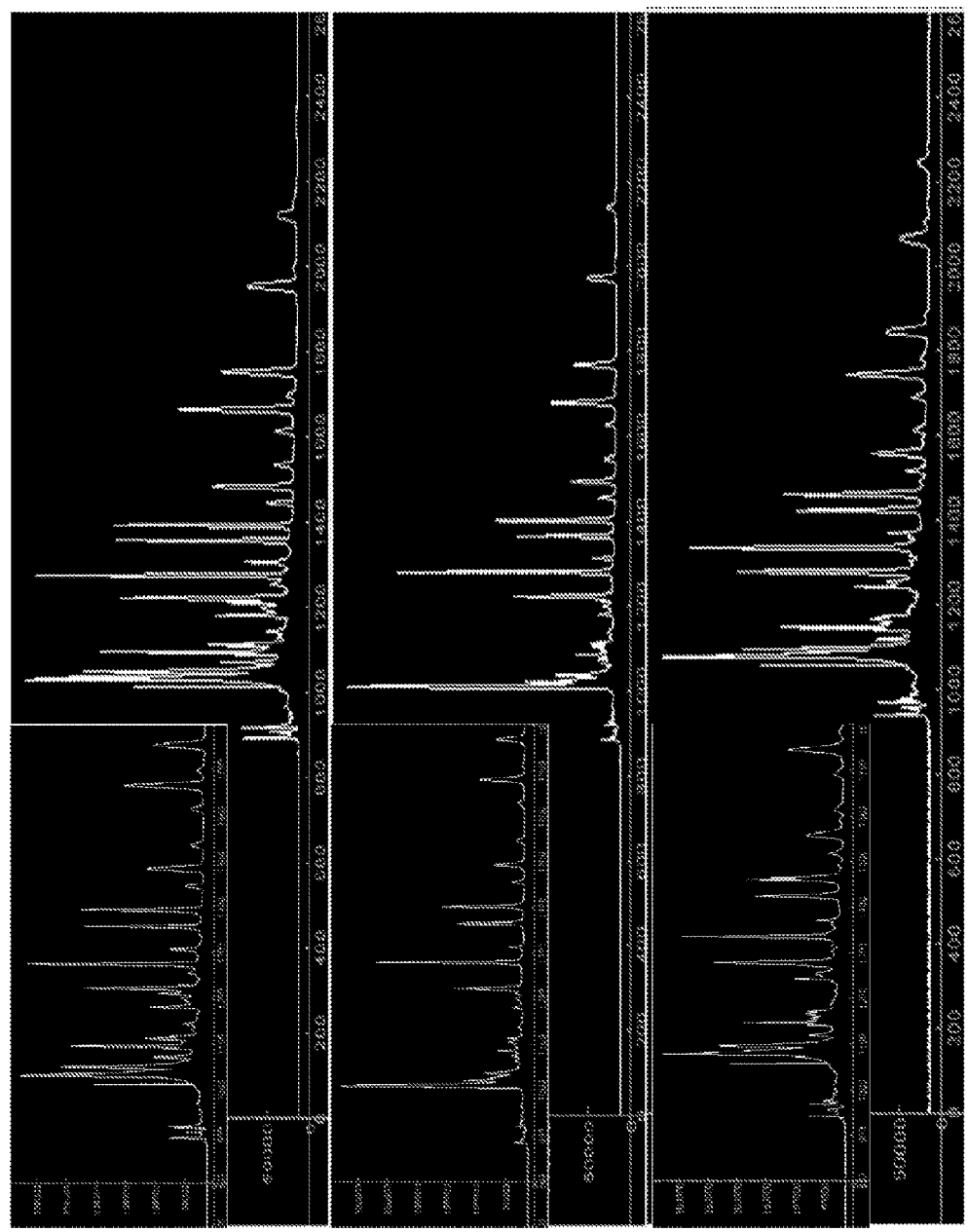
Figure 8D. Result: VQ-all (H06)

REDUCED ARTIFACT DENATURING CAPILLARY ELECTROPHORESIS OF NUCLEIC ACIDS

CROSS-REFERENCE TO RELATED APPLICATIONS

This application is a 35 U.S.C. §371 National Phase Entry Application of International Application No. PCT/US2012/023114 filed Jan. 30, 2012, which designates the U.S., and which claims benefit under 35 U.S.C. §119(e) of U.S. Provisional Patent Application Ser. No. 61/438,070 filed on Jan. 31, 2011, the contents of which are incorporated herein by reference in their entireties.

FIELD OF THE INVENTION

The invention relates to the field of denaturing capillary electrophoresis of nucleic acids.

BACKGROUND OF THE INVENTION

Capillary electrophoresis (CE) has been applied widely as an analytical technique because of several technical advantages: (i) capillaries have high surface-to-volume ratios which permit more efficient heat dissipation which, in turn, permit high electric fields to be used for more rapid separations; (ii) the technique requires minimal sample volumes; (iii) superior resolution of most analytes is attainable; and (iv) the technique is amenable to automation, e.g. Camilleri, editor, Capillary Electrophoresis Theory and Practice (CRC Press, Boca Raton, 1993); and Grossman et al, editors, Capillary Electrophoresis (Academic Press, San Diego, 1992). The need for rapid and accurate separation of nucleic acids, particularly DNA, arises in the analysis of polymerase chain reaction (PCR) products and DNA sequencing fragment analysis, e.g. Williams, Methods 4: 227-232 (1992); Drossman et al, Anal. Chem., 62: 900-903 (1990); Huang et al, Anal. Chem., 64: 2149-2154 (1992); and Swerdlow et al, Nucleic Acids Research, 18: 1415-1419 (1990).

Separation of DNA by denaturing CE with injection from high salt buffers, such as PCR buffer, often generates more than one target-specific peaks: a main peak migrating as single-stranded (ss) DNA and additional, faster-migrating peak or peaks, likely consisting of double-stranded (ds) or partially double-stranded DNA. The appearance of this artifactual peak(s), also referred to herein as a "shadow" or "shadow artifact" peak, presents problems for the assignment of peaks to nucleic acid species in the sample and for the quantitation of individual species therein.

SUMMARY OF THE INVENTION

Described herein are methods for avoiding the incidence or reducing the magnitude of shadow peaks in denaturing nucleic acid capillary electrophoresis (CE). The methods provided herein rely, in part, on steps that remove non-denatured material from the tip of the capillary following electrokinetic injection and before separation of the injected nucleic acids over the capillary. The methods described can be applied in the context of essentially any denaturing nucleic acid capillary electrophoresis using electrokinetic injection for sample loading.

In one aspect, described herein is a method for reducing the magnitude of an artifact peaks in denaturing nucleic acid CE, the method comprising: a) electrokinetically injecting a denatured nucleic acid sample into one end of a CE capillary comprising a denaturing separation medium; b) applying a voltage of the opposite polarity or in the reverse direction to that used to inject the nucleic acid sample into the capillary, the voltage being of a strength and applied for a time sufficient to expel from the capillary at least nucleic acid which has not entered the properly denaturing separation medium; c) after step (b), electrophoretically separating nucleic acid in the capillary using voltage of the same polarity or direction as that applied to electrokinetically inject the nucleic acid sample in step (a), wherein the method reduces the magnitude, impact and relative weight of an artifact peak(s) in the resulting electropherogram relative to the same method lacking step (b).

In one embodiment, the method further comprises, before step (b), the step of transferring the end of the capillary to a reservoir substantially lacking nucleic acid sample.

In another embodiment, step (c) comprises, before the electrophoretically separating step, transferring the end of the capillary to a separate reservoir comprising electrophoresis buffer.

In another embodiment of this and other aspects described herein, the artifact peaks comprise double-stranded DNA.

In another embodiment of this and other aspects described herein, the sample comprises a PCR reaction mixture.

In another embodiment of this and other aspects described herein, the nucleic acid sample substantially lacks formamide.

In another embodiment of this and other aspects described herein, the sample comprises formamide.

In another aspect, described herein is a method for denaturing capillary electrophoretic separation of nucleic acids, the method comprising: a) immersing an end of a CE capillary comprising a denaturing separation medium in a sample comprising nucleic acid; b) applying a voltage along/through the CE capillary for a time and in a direction sufficient to introduce a plug of nucleic acids from the sample into the denaturing separation medium; c) transferring the end of the capillary to a reservoir comprising electrophoresis buffer and applying a voltage along the capillary to effect electrophoretic separation of nucleic acid species in the plug. In this aspect, the improvement comprises: after step (b) and before step (c), applying a voltage in reverse direction relative to that applied in step (b) along the capillary, of a strength and for a time sufficient to expel from the capillary at least nucleic acid which has not entered the denaturing separation medium, whereby relative magnitude of an artifact peak is reduced.

In one embodiment, the method further comprises the step, after step (b) and before step (c), of transferring the end of the capillary to a reservoir substantially lacking nucleic acid sample.

In another aspect, described herein is a method for reducing the magnitude of an artifact peak(s) in denaturing nucleic acid capillary electrophoresis (CE), the method comprising: a) contacting an end of a CE capillary comprising a denaturing separation medium with a nucleic acid sample and applying a voltage along the capillary sufficient to introduce a sample plug containing nucleic acids from the sample into the separation medium in the capillary; b) removing the end of the capillary from step (a) from the sample; and c), after step (b), applying a voltage in reverse direction relative to that applied in step (a) along the capillary, of a strength and for a time sufficient to expel at least a portion of nucleic acid material present at the tip of the capillary which has not entered the functional denaturing separation medium (i.e., has not entered a portion of the separation medium comprising sufficient denaturing agent to maintain denatured status of the denatured nucleic acid molecules introduced—the "functional" denaturing separation medium has denaturing agent at a concentration sufficient to maintain denatured status of introduced denatured nucleic acid); whereby the relative magnitude of an artifact peak is reduced when nucleic acids in the plug are separated by electrophoretic separation of the sample through the capillary.

In one embodiment, the method further comprises the step, after step (b) and before step (c), of immersing the end of the CE capillary in buffer substantially lacking nucleic acid sample.

In another embodiment, the method further comprises the step, after step (c), of transferring the end of the capillary to a reservoir comprising electrophoretic separation buffer and electrophoretically separating nucleic acids in the plug.

In another aspect, described herein is a computer-readable, physical memory comprising computer-executable instructions thereupon for directing an automated capillary electrophoresis device to load and electrophoretically separate nucleic acid molecules in a nucleic acid sample, the instructions comprising: a) instructions to cause the device to immerse an end of a CE capillary into a nucleic acid sample; b) instructions to cause the device to apply a voltage along the capillary for a time sufficient to introduce a plug of nucleic acid molecules from the sample into denaturing separation medium comprised by the capillary; c) instructions to cause the device to move the end of the capillary to a separate reservoir; d) instructions to cause the device to apply a voltage of reverse direction to that applied in step (b) along the capillary for a time and of a strength sufficient to expel nucleic acid material present at the tip of the capillary which has not entered the denaturing separation medium; and e) instructions to cause the device, after step (d) to apply a voltage along the capillary in the direction applied in step (b), to thereby electrophoretically separate nucleic acid molecules introduced to the separation medium.

In one embodiment, the instructions further comprise instructions for, after step (d), and before step (e), transferring the end of the capillary to another reservoir comprising electrophoretic separation medium.

In another aspect, described herein is a system for denaturing capillary electrophoresis, the system comprising: a) a capillary electrophoresis device operatively linked to a computer processor and a robotic device to permit movement of a capillary end from a sample reservoir to one or more additional reservoirs and said CE device; b) a computer-readable, physical memory comprising computer-executable instructions thereupon for directing the capillary electrophoresis device and robotic device to load and electrophoretically separate nucleic acid molecules in a nucleic acid sample, the instructions comprising: i) instructions to cause the robotic device to immerse an end of a CE capillary into a nucleic acid sample; ii) instructions to cause the CE device to apply a voltage along the capillary for a time sufficient to introduce a plug of nucleic acid molecules from the sample into denaturing separation medium comprised by the capillary; iii) instructions to cause the robotic device to move the end of the capillary to a separate reservoir; iv) instructions to cause the CE device to apply a voltage in the reverse direction to that applied in step (ii) along the capillary for a time and of a strength sufficient to expel nucleic acid material present at the tip of the capillary which has not entered the denaturing separation medium; and v) instructions to cause the CE device, after step (iv) to apply a voltage along the capillary in the direction applied in step (ii), to thereby electrophoretically separate nucleic acid molecules introduced to the separation medium.

In one embodiment, the instructions further comprise instructions for, after step (iv), and before step (v), transferring the end of the capillary to another reservoir comprising electrophoretic separation medium.

In another aspect, described herein is a method for reducing the magnitude of an artifact peak(s) in denaturing nucleic acid capillary electrophoresis (CE), the method comprising: a) electrokinetically injecting a nucleic acid sample into one end of a CE capillary comprising a denaturing separation medium; b) transferring the end of the CE capillary to a reservoir of buffer substantially lacking nucleic acid sample, and transiently heating the capillary in an amount and for a time sufficient to cause expansion of the separation medium; and c) after step (b), electrophoretically separating the nucleic acid sample, wherein steps (a)-(c) reduce the relative magnitude of an artifact peak(s) in the resulting separated species. The expansion is preferably of a magnitude sufficient to expel any non-denatured nucleic acids present at the tip of the capillary.

In one embodiment, the transient heating comprises joule heating of the capillary and its contents. It is preferred that the joule heating is achieved by application of reverse-direction voltage relative to the voltage applied to electrokinetically inject the nucleic acid into the capillary.

In another embodiment, the expansion causes the expulsion of at least nucleic acid material present at the tip of the capillary which has not entered the denaturing separation medium.

In another embodiment, the electrophoretic separating step (c) comprises transferring the end of the capillary to a second or additional reservoir comprising electrophoresis buffer.

In another aspect, described herein is a method for denaturing capillary electrophoretic separation of nucleic acids, the method comprising: a) immersing an end of a CE capillary comprising a denaturing separation medium in a sample comprising nucleic acid; b) applying a voltage along the CE capillary for a time and in a direction sufficient to introduce a plug of nucleic acids from the sample into the denaturing separation medium; and c) transferring the end of the capillary to a reservoir comprising electrophoresis buffer and applying a voltage along the capillary to effect electrophoretic separation of nucleic acid species in the plug. In this aspect, the improvement in the method comprises: i) after step (b) and before step (c), transferring the end of the capillary to a reservoir comprising a buffer substantially lacking nucleic acid sample; and ii) heating at least the loaded end of the capillary at a temperature and for a duration sufficient to cause the expansion of the denaturing separation medium, whereby at least material present at the tip of the capillary which has not entered the denaturing separation medium is expelled from the end of the capillary, such that non-denatured nucleic acid from the sample substantially does not enter the separation medium in the capillary, whereby the relative magnitude of an artifact peak is reduced relative to the method performed without steps (i) and (ii).

In one embodiment, the heating in step (ii) comprises joule heating of the capillary. It is preferred that the joule heating is effected by applying a voltage pulse along the capillary in a reverse direction relative to the voltage applied in steps (b) and (c).

In another aspect, described herein is a method for reducing the magnitude of an artifact peak in denaturing nucleic acid capillary electrophoresis (CE), the method comprising:

a) contacting an end of a CE capillary comprising a denaturing separation medium with a nucleic acid sample and applying a voltage along the capillary sufficient to introduce a plug of nucleic acids from the sample into the separation medium in the capillary; b) removing the end of the capillary from step (a) from the sample; and c) after step (b), applying heat to the capillary in an amount and for a time sufficient to cause expansion of the contents of the capillary, the expansion resulting in expulsion of at least material present at the tip of the capillary which has not entered the denaturing separation medium; whereby the magnitude of an artifact peak is reduced when nucleic acids in the plug are separated by electrophoretic separation of the sample through the capillary.

In one embodiment, step (c) comprises joule heating of the capillary. It is preferred that the joule heating is achieved by application of reverse-direction voltage relative to that applied to introduce the plug of nucleic acids into the capillary.

In another embodiment, the method further comprises the step, after step (b) and before step (c) of immersing the end of the CE capillary in buffer substantially lacking nucleic acid sample.

In another embodiment, the method further comprises the step, after step (c), of transferring the end of the capillary to a reservoir comprising electrophoretic separation buffer and electrophoretically separating nucleic acids in the plug.

In another aspect, described herein is a computer-readable, physical memory comprising computer-executable instructions thereupon for directing an automated capillary electrophoresis device to load and electrophoretically separate nucleic acid molecules in a nucleic acid sample, the instructions comprising: a) instructions to cause the device to immerse an end of a CE capillary into a nucleic acid sample; b) instructions to cause the device to apply a voltage along the capillary for a time sufficient to introduce a plug of nucleic acid molecules from the sample into separation medium comprised by the capillary; c) instructions to cause the device to move the end of the capillary to a separate reservoir; d) instructions to cause the device to apply a voltage in the reverse direction to that applied in step (b) along the capillary for a time and of a strength sufficient to expel material present at the tip of the capillary which has not entered the separation medium; and e) instructions to cause the device, after step (d) to apply a voltage along the capillary in the direction applied in step (b), to thereby electrophoretically separate nucleic acid molecules introduced to the separation medium.

In one embodiment, the instructions further comprise instructions for, after step (d), and before step (e), transferring the end of the capillary to another reservoir comprising electrophoretic separation medium.

In another aspect, described herein is a system for denaturing capillary electrophoresis, the system comprising: a) a CE device and a robotic device to permit movement of a capillary end from a sample reservoir to one or more additional reservoirs and to the CE device, both operatively linked to a computer processor; b) a computer-readable, physical memory comprising computer-executable instructions thereupon for directing the capillary electrophoresis device and robotic device to load and electrophoretically separate nucleic acid molecules in a nucleic acid sample, the instructions comprising: i) instructions to cause the robotic device to immerse an end of a CE capillary into a nucleic acid sample; ii) instructions to cause the CE device to apply a voltage along the capillary for a time sufficient to introduce a plug of nucleic acid molecules from the sample into separation medium comprised by the capillary; iii) instructions to cause the robotic device to move the end of the capillary to a separate reservoir; iv) instructions to cause the CE device to apply a voltage in the reverse direction to that applied in step (ii) along the capillary for a time and of a strength sufficient to expel material present at the tip of the capillary which has not entered the separation medium; and v) instructions to cause the CE device, after step (iv) to apply a voltage along the capillary in the direction applied in step (ii), to thereby electrophoretically separate nucleic acid molecules introduced to the separation medium.

In one embodiment of the system, the instructions further comprise instructions for, after step (iv), and before step (v), transferring the end of the capillary to another reservoir comprising electrophoretic separation medium.

As used herein, an "artifact peak" is a signal peak (e.g., a peak of fluorescence signal from a labeled nucleic acid species), detected in a denaturing capillary electrophoresis separation of nucleic acid species, the magnitude or relative position of which can vary depending upon the electrophoresis loading and separation conditions using a given denaturing separation matrix composition. That is, artifact peaks are present when aliquots of the same sample are capillary electrophoresed through the same denaturing separation matrix under different loading and/or separation conditions and peaks either shift locations relative to each other, shift magnitude with respect to each other, or are simply present under one set of loading/separation conditions and not detected under another. As discussed elsewhere herein, a key source of artifact peaks is the presence of either non-denatured or only partially denatured DNA in denaturing CE—because double-stranded DNA tends to migrate faster than single-stranded DNA, the presence of the double stranded form of a given nucleic acid species in the separation results in a split peak or a "shadow" peak migrating ahead of the main peak of single-stranded DNA of a given length.

As used herein, the phrase "reducing the relative magnitude of an artifact peak" refers to a reduction by at least 10% in the magnitude of an artifact capillary electrophoresis signal peak relative to the magnitude of the peak of interest as occurs or is detected under one set of loading and electrophoresis conditions, compared to the relative magnitude of that peak under a reference set of conditions. Generally, the artifact peak magnitudes resulting from a set of CE loading and/or electrophoresis conditions in which steps as described herein for the reduction of artifact peaks are taken would be compared to the magnitudes resulting from loading and separation under the same conditions except where those steps were not undertaken. It is preferred that the magnitude of a given artifact peak, and preferably all similar artifact peaks in a given separation be reduced by at least 20%, at least 30%, at least 40%, at least 50%, at least 60%, at least 70%, at least 80%, at least 90%, at least 95%, at least 98%, at least 99% or more, up to and including the absence of the artifact peak(s) under given detection conditions (e.g., fluorescence detection, where as used herein, signal is not considered "detected" until it is at least twice the background level).

As used herein, the phrase "denaturing separation medium" refers to a CE separation medium that comprises a sufficient amount of a DNA denaturing agent, e.g., urea, to maintain the denatured (i.e., single-stranded) state of denatured DNA that enters and travels through the separation medium. It is noted that a "denaturing separation medium" may contain denaturing agent at a concentration that does not necessarily denature double-stranded DNA but that will prevent the re-formation (or re-naturation) of double stranded form for molecules that are denatured when the sample is applied to the capillary. For a sample to have "entered" denaturing separation medium in a capillary, the concentration of denaturing agent in the part of the separation medium (separation matrix gel) to which the DNA sample has penetrated or migrated must be high enough to prohibit re-naturation of the separated DNA strands. Where, for example, denaturing agent has diffused out of the separation medium at the end of a capillary, producing a gradient of denaturing agent at the capillary tip, denatured DNA sample has not entered the "denaturing separation medium" until it reaches a place in the medium where the denaturing agent is high enough to block re-naturation. Commonly used denaturing separation medium is prepared with 8 M urea. Other denaturing agents compatible with the selected separation medium or matrix can also be used.

As used herein, the term "nucleic acid sample" refers to the nucleic acids in a sample of interest for CE separation and detection of the nucleic acid species therein. A nucleic acid sample as the term is used herein can have from one to thousands or more different nucleic acid species, e.g., DNA molecules.

As used herein, the phrase "substantially lacking nucleic acid sample" refers to a liquid medium, solution or buffer that has either no nucleic acid sample present, or has nucleic acid (or nucleic acid sample) present at levels below the detection threshold for capillary electrophoresis under detection conditions applied in a given CE procedure. Where, for example, the end of a capillary containing electrokinetically injected nucleic acid species from a nucleic acid sample is transferred from the nucleic acid sample reservoir or container to a second reservoir comprising a medium, solution or buffer "substantially lacking nucleic acid sample" prior to heating or applying a reverse-polarity pulse to the capillary as described herein, it is preferred that there be no nucleic acid from that sample in the second reservoir. However, nucleic acid can be present in the second reservoir, e.g., resulting from immersion of prior sample-laden capillary tips in the reservoir or from incomplete rinsing between capillary tip immersions, as long as any amount of nucleic acid from the second reservoir that ends up being separated over the capillary is below the detection threshold, or at or below background signal, for the device for that CE run. While it remains preferred that there be no nucleic acid in a reservoir "substantially lacking nucleic acid sample," in one embodiment such a reservoir can have nucleic acids other than sample nucleic acids; to permit accurate quantitation and band assignment, the sizes of such nucleic acids in the reservoir would need to be different (i.e., electrophoretically resolvable over the CE capillary) from those of species of interest in the sample to be separated.

As used herein, the phrase "transiently heating" a capillary "in an amount and for a time sufficient to cause expansion of said separation medium" refers to the application of heat to at least a portion of a CE capillary sufficient to expand separation medium in the capillary—the expansion would, for example, push liquid present at the tip of the capillary out of the capillary and into the surrounding medium, solution or buffer. The heating can be localized, e.g., near the sample-injection tip of the capillary, or at some other relatively narrow location over the length of the capillary—it is generally to be expected that expansion of the matrix at some distance from either end of the capillary would generate pressure sufficient to push liquid from the end of the capillary, as gel in a capillary is not readily compressed. Alternatively, the heating can be more generalized or over a broad portion of the capillary. The heating can be "transient" in that it is not maintained during the separation phase of the CE run. Times for transient heating can vary with the manner and degree of heating, but will generally be on the order of several seconds (e.g., 3 seconds, 5 seconds, 7 seconds, 10 seconds or more) to about 1 minute. Temperatures applied in the transient heating can vary, but should be less than 100° C., e.g., 95° C., 90° C., 88° C., 85° C., 83° C., 80° C., 78° C., 75° C., 73° C., 70° C., 68° C., 65° C., 63° C., 60° C. or less, but will generally be greater than about 40° C. The ordinarily skilled artisan can determine a combination of time and temperature that works using no more than routine experimentation. While it is preferred that heating is transient, continuous heating is also contemplated, such that a temperature greater than the Tm of at least the species of interest in a given sample is maintained throughout the separation.

As used herein, the phrase "joule heating" refers to the heating of a conductive material, e.g., a CE separation medium, by running an electric current through it.

As used herein, the phrase "reverse-polarity" refers to a voltage applied in the opposite direction to a reference. In the context of the methods described herein, reverse-polarity voltage is applied after electrokinetic injection of a nucleic acid sample into a CE capillary, with polarity opposite that applied to electrokinetically inject the sample. The term "reverse direction" is used interchangeably with reverse-polarity herein.

As used herein, the phrase "substantially lacks formamide" means that the nucleic acid sample loaded onto a CE capillary either completely lacks formamide or lacks a concentration of formamide sufficient to properly or fully denature DNA in the sample. Formamide-based nucleic acid loading solutions for CE tend to provide final concentrations of 10% formamide or more, including, for example, 13.3% or more, 15% or more, 25% or more, 50% or more, 60% or more, 70% or more, or even 80% or more 80% formamide or more. It is preferred that a sample that "substantially lacks" formamide have no formamide present, but in particular embodiments, formamide can be present at less than 10%, preferably less than 5%, more preferably less than 2%, more preferably less than 1%. Where the sample is a PCR reaction mixture, it is preferred that there be no formamide present in the reaction mixture. In some embodiments, formamide can be added to a sample taken from a PCR reaction as a denaturant prior to loading onto a CE capillary, but it is emphasized that using the methods described herein can avoid or reduce the magnitude of shadow artifacts on CE of PCR samples, without the use of formamide loading buffers.

BRIEF DESCRIPTION OF THE FIGURES

FIG. 1 shows an example of a capillary electrophoresis separation preformed on samples taken at various times during a multiplex PCR amplification. NSA 95, with the white arrow indicating a non-specific amplicon migrating at 95 nucleotides. Remaining gray arrows indicate shadow artifact bands.

FIG. 2 shows a schematic of a CE set-up, including a capillary comprising denaturing separation medium, within a thermostatically controlled cartridge body, with protruding sample loading (cathode) and non-sample-loading (anode) ends. The sample-loading end is arranged in a holder to permit immersion in a sample of heated DNA. Robotic elements for transferring the loading end of the capillary from one location to another are not shown.

FIG. 3 shows the results of CE where separation is performed at increasing temperatures from 27° C., to 35° C., 45° C. and 55° C. The arrows mark the location of the shadow peak(s).

FIG. 4 shows the results of CE where separation is performed at one temperature following injection temperatures including 35° C., 55° C., 60° C., and 85° C. The locations of NSA 95, main and shadow peaks are indicated.

FIG. 5 shows the results of CE in which injection was performed at 85° C. and 95° C.

FIGS. 6A-6H show schematics of one series of injection-related events postulated to occur in the capillary and at the sample-loading capillary tip. The invention is not intended to be limited by theory; however, the following illustrates a proposed series of events leading to shadow formation. FIG. 6A shows the capillary prior to injection. A blow-up of the capillary tip is shown, with CE gel (denaturing CE separation medium) and the interface between the gel and the surrounding medium indicated. FIG. 6B shows the situation at the capillary tip at the start of injection. It is postulated that the CE gel heats up and expands as the injection current runs through it. The expansion extrudes a small amount of the gel into the sample. During the injection, shown further in FIG. 6C, denatured DNA electrokinetically flows into the capillary gel matrix (shown in large black circles). FIG. 6D shows the situation postulated after injection is complete—cooling of the capillary matrix permits it to contract. A plug of denatured DNA (single stranded, or ssDNA) has entered the denaturing separation medium, and the contraction of the gel in the capillary leaves a void at the tip of the capillary that is filled with sample solution. As it cools, ssDNA in the sample solution at the tip of the gel can re-nature to form dsDNA, shown in a brick pattern. Urea denaturing agent in the gel prevents the re-naturation of ssDNA that has entered the gel. FIG. 6E shows the situation postulated to occur as the tip of the capillary is moved from the sample to the buffer reservoir for separation. ssDNA and dsDNA are present at the tip. FIGS. 6F and 6G show the situation postulated to occur as separation is performed. dsDNA enters the gel as separating voltage is applied. The urea in the gel, while sufficient to prevent renaturation of the ssDNA is not able to denature DNA that is double stranded when it enters the gel at ambient temperature. The dsDNA migrates faster, overtaking the ssDNA in the main peak to form a shadow peak. FIG. 6H shows events postulated to occur as the migrating DNA enters the heated (thermostated) portion of the capillary—depending upon the temperature of the cartridge, the dsDNA is postulated to either denature to ssDNA (a brick pattern), which will form a split peak, or remain double-stranded, which will retain the shadow peak. Slower-migrating ssDNA (large black circles) remains single stranded throughout the separation.

FIG. 7 shows a schematic of an alternative (or coincident) series of injection-related events postulated to occur in the capillary and at the sample-loading capillary tip. The invention is not intended to be limited by theory; however, the following illustrates a proposed series of events contributing to shadow formation. FIG. 7 shows the capillary after injection—as the capillary cools following injection, there is ssDNA that has entered the denaturing separation medium (shown in black dots) and DNA which has entered a zone of the gel at the interface in which the denaturing agent is diluted, and where re-naturation becomes possible (shown in horizontal stripes). Once the non-denatured DNA enters the gel, shadow and/or split peaks are possible as diagrammed in FIG. 6.

FIGS. 8A-8D show results of application of no pulse, an RP pulse and a "normal" pulse on different single and multiplex amplification products. In FIG. 8A, a single-plex reaction is shown. FIG. 8B shows the results of a similar experiment with a 3-plex PCR reaction product. FIGS. 8C and 8D show the results of RP and "normal" pulsing relative to no pulse for two different hi-order multiplex amplification reactions.

DETAILED DESCRIPTION

Denaturing capillary electrophoresis separation of DNA with injection from high salt buffers, such as PCR buffer often generates more than one target-specific peak: a main peak migrating as single-stranded (ss) DNA and additional, faster-migrating peak(s), likely comprising double-stranded (ds) or partially double-stranded DNA. The appearance of such additional, artifactual peak(s), also referred to herein as "shadow" or "shadow artifact" peak(s), presents problems for the assignment of peaks to nucleic acid species in the sample, and for the quantitation of individual species therein.

Described herein are methods for avoiding or reducing the magnitude of shadow peaks. In one aspect, the methods described herein involve a step or steps taken after electrokinetic injection of DNA into a capillary to dismiss from the capillary tip DNA that has not entered the denaturing separation medium before beginning separation of nucleic acid species over the capillary. Without wishing to be bound by theory, it is thought that the removal of such material from the tip of the capillary can prevent non-denatured DNA from entering the capillary and forming shadow artifact peaks. Such approaches are broadly applicable to any denaturing nucleic acid CE separation in which shadow artifact peaks occur. They are particularly well suited for denaturing nucleic acid CE separation of PCR reaction products, in that they do not require, for example, the use of agents, such as formamide, that can interfere with the PCR reaction. This permits the sampling of PCR reactions at repeated instances during cycling, which, when combined with CE separation provides not only the generation of an amplification profile for amplicons over the course of the reaction, but permits monitoring of multiple species in multiplex amplifications by size differentiation of the respective amplicon products. While not absolutely necessary, injection of nucleic acid sample into denaturing separation medium in a CE capillary is preferably performed while the nucleic acids in the sample are denatured. For injection directly from a PCR reaction, this can mean that sample is injected during the strand-separation step most commonly performed at between 92° C. and 95° C. Where injection is not directly from a PCR or other reaction mixture, heat and/or agents such as formamide can be used to denature the DNA prior to electrokinetic injection onto the capillary.

In one embodiment, the methods comprise applying a reverse-polarity pulse after the electrokinetic injection step and before electrophoretic separation of the injected sample. While not wishing to be bound by theory, it is thought that a brief reverse-polarity pulse can eject non-denatured (or re-natured) DNA present at the capillary tip, either in a space at the end of the tip or in a zone of the gel matrix in which the denaturing agent has become diluted. The reverse polarity pulse is sufficient to expel non-denatured DNA from the end of the capillary, but is of a duration and of a strength such that denatured sample nucleic acids which did enter the denaturing separation medium in the capillary are retained, to be separated in the subsequent electrophoresis step. It is preferred that the reverse-polarity pulse is applied after the capillary tip is removed from the nucleic acid sample, such that re-entry of non-denatured DNA does not occur, and further preferred that the pulse is applied when the tip is immersed in a second or separate reservoir of solution or buffer substantially lacking nucleic acid sample, as that phrase is defined herein.

In this aspect, the duration and strength of the reverse polarity pulse can vary. It should be clear to one of ordinary skill in the art that the longer the pulse, the more of the injected nucleic acid (both non-denatured and denatured) will be expelled, and the stronger the pulse, the more will be expelled. Thus, the amount of the injected material or material present at the tip of the capillary that is expelled from the tip is directly related to the duration and strength of the reverse polarity pulse. Thus, a relatively weak pulse for a longer duration can work, as can a very strong pulse for a relatively short duration. As a general rule of thumb, it has been found that conditions that "unload" about half of the injected material work best to balance the reduction in shadow artifacts with good nucleic acid detection and resolution. Without wishing to be limited to a specific set of conditions, it has been found that injection at 10 kV for 15 seconds works well with a reverse polarity pulse at 15 kV for 3 seconds. It is noted that the optimal time and strength of reverse-polarity pulsing can be affected to some extent by differences in CE buffer formulations, although it is not expected that differences will be dramatic, especially for commonly used buffer formulations. It is expected that the ordinarily skilled artisan can determine a set of strength and duration conditions that will work with a given buffer formulation with a minimum of experimentation. It is further noted that the salt or buffer composition of the sample can affect injection characteristics. However, the reverse-polarity approaches described herein have been found to work in the context of injection from both standard sample conditions, e.g., sample in PCR buffer, as well as in the context of injection from non-ionic solvent, e.g., formamide, as demonstrated herein.

For the injection, it is easy to trade time for voltage, with very little effect on the results. For the reverse polarity step, shorter pulses with high voltage tend to work better for shadow suppression than longer pulses with lower voltage. Thus, while the system used for these experiments has a maximum voltage of 15 kV, voltages higher than 15 kV may work better for the reverse polarity pulse, with corresponding reductions in time as needed. Thus, for example, voltages as high as 17 kV, 18 kV, 20 kV, 22 kV, 24 kV, 26 kV or more can be useful in the methods described herein.

In another embodiment, the methods comprise transiently treating the capillary, after electrokinetic sample injection, and before electrophoretic separation of the injected sample, in a manner sufficient to cause the expansion of the denaturing separation matrix, e.g., by transiently heating all or a portion of the separation matrix. While not wishing to be bound by theory, it is thought that the expansion can physically expel non-denatured DNA present at the tip of the capillary that has not entered the denaturing separation medium. The treatment should occur after the capillary has been removed from the nucleic acid sample (e.g., from a PCR reaction) to avoid the re-entry of non-denatured DNA after expulsion, and is preferably performed while the capillary tip is immersed in a reservoir of solution substantially lacking sample nucleic acid. While the denaturing separation medium or matrix in the capillary is sufficient to maintain the denatured state of DNA that is denatured when loaded, it is not necessarily sufficient to denature DNA that is not denatured when it enters the capillary. Thus, the expansion of the matrix and expulsion of non-denatured DNA at the tip of the capillary after injection removes the double-stranded DNA that could otherwise result in shadow peak formation when the electrophoretic separation is performed.

A treatment sufficient to cause expansion of the denaturing separation matrix in the capillary can include, in some embodiments, for example, transiently heating all or a portion of the capillary at a temperature and for a time sufficient to cause the matrix to expand. Because the separation matrix is not compressible, heating at essentially any point along the length of the capillary will cause the matrix to expand at that point and cause pressure over the length of the capillary that can ultimately result in expulsion of material at the tip of the capillary, including non-denatured DNA. It is preferred that the heat transiently applied is greater than the thermostatically set temperature of the CE cartridge body during the injection or separation steps of CE. The temperature applied can vary, so long as expansion of the separation medium occurs sufficient to achieve the desired expulsion of non-denatured DNA. However, temperatures will generally be less than 100° C., e.g., e.g., 95° C., 90° C., 88° C., 85° C., 83° C., 80° C., 78° C., 75° C., 73° C., 70° C., 68° C., 65° C., 63° C., 60° C., or less, but will generally be greater than about 40° C.

Heating of the matrix can be achieved by, in some embodiments, for example, a thermostatically-controlled heating element in contact with a portion of the capillary. The element can be controlled by a microprocessor. In one embodiment, the heating element can be a Peltier-type solid state heating element—such an element is useful in that Peltier heating is rapid and easily controlled, and the footprint or space requirements for efficient Peltier-type heating elements are commonly smaller than other types of elements.

The transient heating can be achieved by Joule heating, i.e., heating caused by passing a current through the separation matrix in the capillary. However, if Joule heating is used, the current should be of the opposite direction relative to the current used to inject the sample—otherwise, the heating effect will likely be offset by the entry of the non-denatured DNA, initially at the tip of the capillary, further into the separation matrix. Non-denatured DNA in the separation matrix would then form shadow peaks during the separation phase of the CE process. Joule heating via reverse-polarity pulse can be performed as described in the Examples herein, and the ordinarily skilled artisan can generally determine the strength and duration of the current (or a range thereof) necessary to heat and expand the matrix so as to expel non-denatured material present at the tip of the capillary after injection. In general, it is expected that heating necessary for this purpose can be achieved by a pulse of voltage on the order of 10 kV or more, e.g., 12 kV, 14 kV, 15 kV, 16 kV, 17 kV, 18 kV, 20 kV, 22 kV, 24 kV, 26 kV, or more. The corresponding duration of the Joule heating pulse will decrease with increasing voltage, however, a time of about 5-7 seconds for a pulse of 10 kV provides a reasonable starting point following injection at 10 kV for 15 seconds. The application of reverse-polarity voltage of 15 kV for 3 seconds following sample injection at 10 kV for 15 seconds works well for this aspect. The ordinarily skilled artisan can readily determine with routine experimentation the Joule heating pulse conditions that work in a given system.

In relation to the transient heating of at least a portion of the capillary after electrokinetic injection to reduce shadow artifacts, some additional points can be considered. First, to the extent that the shadow artifacts are caused by cooling of the loaded tip during transfer of the tip from the sample to the reservoir for electrophoretic separation, whether the cooling causes contraction or whether the cooling permits partial re-naturation, or both, it is specifically contemplated that maintaining the temperature of the loaded tip at a temperature that does not permit re-naturation (i.e., a temperature greater than the $T_m$ of the nucleic acid species) during the transfer period and any other delay before separation through the denaturing separation medium can begin, can limit or avoid shadow peaks, possibly without the need for additional heating or reverse polarity pulsing, in some embodiments. Alternatively, it is contemplated that a combination of such temperature maintenance and reverse-polarity pulsing can be employed to further reduce or eliminate the incidence and/or magnitude of shadow peaks, in some embodiments. In one approach, then, maintenance of temperature greater than the $T_m$ of at least the species of interest throughout the loading, transfer and separation steps has similar effect.

Further still, it is contemplated that simply heating the loaded tip of the capillary to a temperature greater than the $T_m$ of the nucleic acid immediately before separation begins would have the effect of denaturing any partially or fully re-natured species in the loaded tip, in some embodiments. This effect would be separate from or in addition to the expansion/expulsion effect discussed elsewhere herein. One approach for doing so would be to heat the electrophoresis buffer reservoir to a temperature above the $T_m$ of the nucleic acid species. Under this approach, even if there is some re-naturation during tip transfer after sample injection, the strands would become denatured again at the time electrophoresis is started and each species would migrate as a single peak. Under this approach, steps should be taken to avoid evaporation from the heated buffer reservoir. Such steps can include, for example, including a tight-fitting cover on the reservoir—the cover itself can be heated to avoid condensation and reflux. Such a cover includes a design that permits the loaded capillary tips to be introduced to the reservoir, e.g., through or around the cover. In one embodiment, the cover can be removed or shifted to permit loaded capillary ends to be placed in the heated buffer reservoir, with the cover being subsequently moved back into position for sample separation. As an alternative to a cover, it is contemplated that the heated reservoir for electrophoresis buffer can be overlaid with, for example, mineral oil or wax.

An alternative to heating the electrophoresis buffer reservoir to a temperature greater that the $T_m$ of the nucleic acid species is to bring the loaded tips into contact or at least close proximity with a heated block immediately prior to immersion in the electrophoresis buffer reservoir. The heated block can be, for example, just above the surface of the buffer. The block would advantageously be heated by Peltier heating, which permits rapid, controlled heating of the block—if the block heats rapidly, it need not be maintained at temperature throughout the run. Heating the block only when needed to heat the loaded tips before immersion can limit problems with the block causing evaporation of the nearby electrophoresis buffer.

Additional considerations for the methods described herein for reducing or preventing CE artifacts, particularly shadow-type artifacts, are described herein below and in the Examples that follow.

Capillary Electrophoresis:

Denaturing capillary electrophoresis is well known to those of ordinary skill in the art. Briefly, a nucleic acid sample is injected from sample at the inlet end of the capillary, into denaturing separation medium in the capillary, and an electric field is applied to the capillary ends. The different nucleic acid components in a sample, e.g., a PCR reaction mixture or other sample, migrate to the detector point with different velocities due to differences in their electrophoretic properties. Consequently, they reach the detector (usually a UV or fluorescence detector) at different times. Results present as a series of detected peaks, where each peak represents ideally one nucleic acid component or species of the sample. Peak area or peak height indicates the initial concentration of the component in the mixture.

CE capillaries themselves are frequently quartz, although other materials known to those of skill in the art can be used.

There are a number of CE systems available commercially, having both single and multiple-capillary capabilities. The methods described herein are applicable to any device or system for denaturing CE of nucleic acid samples. Non-limiting examples of CE devices to which the methods described herein for avoiding or reducing artifact peaks can be applied include the Applied Biosystems, Inc. (ABI) genetic analyzer models 310 (single capillary), 3130 (4 capillary), 3130xL (16 capillary), 3500 (8 capillary), 3500xL (24 capillary), 3730 (48 capillary), and 3730xL (96 capillary), the Agilent 7100 device, Prince Technologies, Inc.'s PrinCE™ Capillary Electrophoresis System, Lumex, Inc.'s Capel-105™ CE system, and Beckman Coulter's P/ACE™ MDQ systems, among others.

While the methods described herein can potentially be of use in microfluidic separations (in which separation is performed through micro-channels etched into or onto glass, silicon or other substrate), in a preferred embodiment, the methods do not comprise microfluidic separation, but employ, rather, separation through single or multiple cylindrical capillary tubes on the order of 10-60 cm or more in length.

Since the charge-to-frictional drag ratio is the same for different sized polynucleotides in free solution, electrophoretic separation requires the presence of a sieving medium. Applicable sieving media include gels, however non-gel liquid polymers such as linear polyacrylamide, hydroxyalkylcellulose (HEC), agarose, and cellulose acetate, and the like can be used. Other separation media that can be used for capillary electrophoresis include, but are not limited to, water soluble polymers such as poly(N,N'-dimethylacrylamide)(PDMA), polyethylene glycol (PEG), poly(vinylpyrrolidone) (PVP), polyethylene oxide, polysaccharides and pluronic polyols; various poly(vinylalcohol) (PVAL)-related polymers, polyether-water mixture, lyotropic polymer liquid crystals, among others. See, for example, the separation media described in Liu et al., 162 *Capillary Electrophoresis of Nucleic Acids: Volume I: Introduction to the Capillary Electrophoresis of Nucleic Acids.* 203 (2000), and the separation media described in Guttaman et al. 22 *LCGC North America* 896 (2004), and Sunada, W. M. et al., 18 *Electrophoresis* 2243 (1997), each of which are incorporated herein by reference.

Other non-limiting examples of separation media for capillary electrophoresis include those disclosed in U.S. Pat. Nos.: 5,569,364, 5,567,292, 5,019,232, 6,001,232, 5,290, 418, 5,213,669, 5,264,101, 5,164,055, 5,151,464, 5,126,021, 4,769,408, 4,582,868 and US Patent App. Pub. No.: 2009/0214638, the contents of which are incorporated herein by reference in their entireties.

Applicable CE separation matrices are compatible with the presence of denaturing agents necessary for denaturing nucleic acid CE, a common example of which is 8M urea.

The magnitude of any given peak, including an artifact peak, is most often determined optically on the basis of either UV absorption by nucleic acids, e.g., DNA, or by fluorescence emission from one or more labels associated with the nucleic acid. UV and fluorescence detectors applicable to nucleic acid CE detection are well known in the art.

To determine whether a method as described herein has reduced the magnitude of an artifact peak relative to the CE performed under the same conditions without the steps described herein to reduce artifact peaks, the skilled artisan would run the CE on separate aliquots of the same sample under both sets of conditions (i.e., with, and without the steps described herein to reduce shadow peak artifacts) and compare the positions and magnitudes of the separated species. Where bands shift in magnitude or in position between the two CE separations, changes in artifact peaks are determined.

Systems

In one aspect, a system is provided herein for the separation and detection of nucleic acids in a sample, the system permitting improved band assignment and quantitation by implementing steps as described herein to reduce the incidence or magnitude of shadow artifact peaks. In particular, provided herein are CE systems in which, following electrokinetic injection of heat-denatured nucleic acid sample, either a reverse-polarity pulse is briefly applied, or at least a portion of the capillary is transiently heated, or both (including, for example, where a reverse-polarity pulse heats the separation medium and capillary), prior to separation using current in the same direction used for injection. It is preferred that the systems described herein are microprocessor-controlled and automated to permit the electrokinetic loading from a sample, reverse polarity pulsing and/or heating, and separation steps in particular that are necessary to perform the methods described. It is also preferred that the system comprise hardware sufficient to effect the transfer of a capillary end from a sample reservoir where nucleic acid is injected, to a CE separation unit, where a reverse polarity pulse and/or heat is applied to the capillary before electrophoretic separation of injected nucleic acids. More preferably the system will comprise hardware sufficient to effect the transfer of a capillary end from a sample reservoir where nucleic acid is injected, to a separate reservoir during reverse-polarity pulsing or heat-treatment of the capillary, and then to a CE separation unit for electrophoretic separation of injected nucleic acids. The system can be contained in a single housing, for convenience, for maintaining a controlled temperature and for minimizing opportunities for contamination. Transfer of the capillary end(s) from sample to CE separation unit or from sample to separate reservoir to CE separation unit can be readily effected with any of a number of robotic instruments that can move a capillary end in the x, y and z directions as necessary for the methods described herein. The process of sample injection, capillary transfer, reverse-polarity or heat application and capillary transfer to the CE separation unit is preferably automated.

In one embodiment, then, a system will comprise a computer processor and a computer-readable physical or tangible memory comprising computer-executable instructions thereupon which direct the system to perform the steps described herein for denaturing nucleic acid CE, including steps as described herein for reducing the incidence or magnitude of artifact peaks, e.g., shadow artifact peaks. It is preferred that the computer-readable memory is a physical computer-readable memory, i.e., not a signal. Computer processors capable of executing instructions as described are well known in the art, as are processor/actuator linkages that permit the automation of the steps described herein that accomplish denaturing nucleic acid CE with reduced artifacts.

At a minimum, the system will comprise the following:
a. a capillary electrophoresis (CE) device operatively linked to a computer processor and to a robotic device capable of moving capillary end(s) in the x, y and z dimensions from sample reservoir(s) to one or more additional reservoirs, including a buffer reservoir of a CE separation unit;
b. a computer-readable, physical or tangible memory comprising computer-executable instructions thereupon for directing the capillary electrophoresis device to load and electrophoretically separate nucleic acid molecules in a nucleic acid sample, wherein the instructions can be arranged in functional modules, comprising:
  i. a first transfer module comprising instructions to cause the robotic device to immerse an end of a CE capillary into a nucleic acid sample;
  ii. a loading module comprising instructions to cause the CE device to apply a voltage along the capillary for a time sufficient to introduce a plug of nucleic acid molecules from said sample into denaturing separation medium comprised by the capillary;
  iii. a second transfer module comprising instructions to cause the robot device to move the loaded end of the capillary to a separate reservoir;
  iv. a reverse-polarity module comprising instructions to cause the CE device to apply a voltage of reverse polarity to that applied in step (ii) along the capillary for a time and of a strength sufficient to expel material present at the loaded tip of the capillary which has not entered the denaturing separation medium; and
  v. a separation module comprising instructions to cause the device, after step (iv) to apply a voltage along the capillary in the direction applied in step (ii), to thereby electrophoretically separate nucleic acid molecules introduced to the denaturing separation medium.

In one embodiment, the separation module instructions include instructions for, after step (iv), and before step (v), transferring the end of said capillary to another reservoir comprising electrophoretic separation medium.

The CE device will comprise, at a minimum, a power supply, a holder for capillaries, and two electrophoresis buffer reservoirs, one at each end of the mounted capillary (ies). The CE device will have the capacity to apply voltage from the power supply in either direction (i.e., forward and reverse polarity), preferably as a programmable routine—i.e., it is preferred that switching from forward to reverse polarity is accomplished without the user needing to intervene at the time. The device will also generally include a detector operably linked to a portion of the capillary(ies) distal to the loading tip of the capillary(ies).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media can be any available tangible or physical media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), USB memory, a hard disk, flash memory or other memory technology, tablet devices, smartphone devices, CD-ROM (compact disc read only memory), DVDs (digital versatile disks) or other optical storage media, transmission media such as those supporting the Internet or an intranet magnetic cassettes, magnetic tape, magnetic disk storage or other magnetic storage media, other types of volatile and non-volatile memory, and any other tangible medium which can be used to store the desired information and which can accessed by a computer, including any suitable combination of the foregoing. As used herein, computer readable storage media or a computer-readable physical memory does not include, for example, non-tangible, transitory forms of signal transmission, such as radio broadcasts, electrical signals, light pulses, carrier waves, and the like.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the media and systems described herein include, at a minimum, a loading module (10) directing sample injection, a transfer module (20) directing transfer of the loaded capillary to a separate reservoir, a reverse-polarity module (30) directing the application of a reverse-polarity pulse, and a separation module (40).

The loading module (1) can comprise a set of instructions for controlling or directing the electrokinetic injection of a sample from a sample reservoir into a CE capillary. Microprocessor-controlled systems adapted for electrokinetic injection of nucleic acids into CE capillaries are well known to those of skill in the art.

Transfer module (20) can comprise a set of instructions to direct a robotic transfer device to effect the transfer of a loaded capillary tip from one reservoir to another. Microprocessor-controlled robotic devices and software sufficient for this purpose are well known in the art, and permit translation of the loaded tip in the x, y and z dimensions to specified locations.

The reverse polarity module (30) can comprise a system and/or set of instructions that permits or directs the reversal of the direction of current output from the CE power supply, and the timed and controlled application of voltage in the reverse direction relative to voltage applied per instruction of the loading module.

The separation module (40) can comprise a system and/or set of instructions that direct the controlled application of "forward" direction voltage, i.e., voltage in the same direction as applied per instruction of the loading module, along the CE capillary to effect separation of loaded sample after reverse-polarity pulsing.

In another embodiment, the reverse polarity module (30) is replaced by or supplemented with a heating module (50). The heating module should direct a microprocessor controlled heating element, including any type of resistive heating element, or a Peltier-type heating element, for example. The heating module directs the transient application of heat to a desired temperature or temperature range to a CE capillary on or connected to the CE device.

Clearly, the detector for the CE device can also be microprocessor-controlled or otherwise interfaced. Hardware and software configurations for detection of separated CE products are well known in the art.

The present invention therefore provides for systems (and computer readable media for causing computer systems) to perform methods for capillary electrophoresis with reduced artifacts.

Systems and computer readable media described herein are merely illustrative embodiments of the invention for performing capillary electrophoresis with reduced artifacts, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

Some aspects and embodiments disclosed herein can be illustrated by, for example any of the following numbered paragraphs:

1. A method for reducing the magnitude of an artifact peak in denaturing nucleic acid capillary electrophoresis (CE), the method comprising:
   a) electrokinetically injecting a nucleic acid sample into one end of a CE capillary comprising a denaturing separation medium;
   b) applying a voltage of the opposite polarity to that used to inject said nucleic acid sample to said capillary, said voltage being of a strength and applied for a time sufficient to expel from said capillary nucleic acid which has not entered said denaturing separation medium;
   c) after step (b), electrophoretically separating nucleic acid in said capillary using a voltage in the same direction as that applied to electrokinetically inject said nucleic acid sample in step (a), wherein steps (a)-(c) reduce the magnitude of an artifact peak in the resulting separated species.

2. The method of paragraph 1, further comprising, before step (b), transferring said end of said capillary to a reservoir substantially lacking said nucleic acid sample.

3. The method of paragraph 1, wherein step (c) comprises, before said electrophoretically separating, transferring said end of said capillary to a separate reservoir comprising electrophoresis buffer.

4. The method of paragraph 1, wherein said artifact peaks comprise double-stranded DNA.

5. The method of paragraph 1, wherein said nucleic acid sample comprises a PCR reaction mixture.

6. The method of paragraph 1, wherein said nucleic acid sample substantially lacks formamide.

7. The method of paragraph 1, wherein said sample comprises formamide.

8. In a method for denaturing capillary electrophoretic separation of nucleic acids, the method comprising:
   a) immersing an end of a CE capillary comprising a denaturing separation medium in a sample comprising nucleic acid;
   b) applying a voltage along said CE capillary for a time and in a direction sufficient to introduce a plug of nucleic acids from said sample into said denaturing separation medium;
   c) transferring said end of said capillary to a reservoir comprising electrophoresis buffer and applying a voltage along said capillary to effect electrophoretic separation of nucleic acid species in said plug;
   the improvement comprising:
   after step (b) and before step (c), applying a voltage in reverse polarity relative to that applied in step (b) along said capillary, of a strength and for a time sufficient to expel from said capillary nucleic acid which has not entered said denaturing separation medium,
   whereby relative magnitude of an artifact peak is reduced.

9. The method of paragraph 8, further comprising, after step (b) and before step (i) the step of transferring said end of said capillary to a reservoir substantially lacking said nucleic acid sample.

10. The method of paragraph 8, wherein said artifact peak comprises double-stranded DNA.

11. The method of paragraph 8, wherein said nucleic acid sample comprises a PCR reaction mixture.

12. The method of paragraph 8, wherein said nucleic acid sample substantially lacks formamide.

13. The method of paragraph 8, wherein said nucleic acid sample comprises formamide.

14. A method for reducing the magnitude of an artifact peak in denaturing nucleic acid capillary electrophoresis (CE), the method comprising:
   a) contacting an end of a CE capillary comprising a denaturing separation medium with a nucleic acid sample and applying a voltage along said capillary sufficient to introduce a plug of nucleic acids from said sample into the separation medium in said capillary;
   b) removing the end of said capillary from step (a) from said sample; and
   c) after step (b), applying a voltage in reverse polarity relative to that applied in step (a) along said capillary, of a strength and for a time sufficient to expel at least a portion of nucleic acid material present at the tip of said capillary which has not entered said denaturing separation medium;
   whereby the relative magnitude of an artifact peak is reduced when nucleic acids in said plug are separated by electrophoretic separation of said sample through said capillary.

15. The method of paragraph 14, wherein said artifact peak comprises double-stranded DNA.

16. The method of paragraph 14, further comprising the step, after step (b) and before step (c) of immersing said end of said CE capillary in buffer substantially lacking nucleic acid sample.

17. The method of paragraph 14, further comprising, after step (c), the step of transferring said end of said capillary to a reservoir comprising electrophoretic separation buffer and electrophoretically separating nucleic acids in said plug.

18. The method of paragraph 14, wherein said nucleic acid sample comprises a PCR reaction mixture.

19. The method of paragraph 14, wherein said nucleic acid sample substantially lacks formamide.

20. The method of paragraph 14, wherein said nucleic acid sample comprises formamide.

21. A computer-readable, physical memory comprising computer-executable instructions thereupon for directing an automated capillary electrophoresis device to load and electrophoretically separate nucleic acid molecules in a nucleic acid sample, said instructions comprising:
   a) instructions to cause said device to immerse an end of a CE capillary into a nucleic acid sample;
   b) instructions to cause said device to apply a voltage along said capillary for a time sufficient to introduce a plug of nucleic acid molecules from said sample into denaturing separation medium comprised by said capillary;
   c) instructions to cause said device to move said end of said capillary to a separate reservoir;
   d) instructions to cause said device to apply a voltage of reverse polarity to that applied in step (b) along said capillary for a time and of a strength sufficient to expel nucleic acid material present at the tip of said capillary which has not entered said denaturing separation medium; and
   e) instructions to cause said device, after step (d) to apply a voltage along said capillary in the direction applied in step (b), to thereby electrophoretically separate nucleic acid molecules introduced to said separation medium.

22. The computer-readable medium of paragraph 21, wherein said instructions further comprise instructions for, after step (d), and before step (e), transferring said end of said capillary to another reservoir comprising electrophoretic separation medium.

23. A system for denaturing capillary electrophoresis, the system comprising
   a) a capillary electrophoresis device operatively linked to a computer processor;
   b) a computer-readable, physical memory comprising computer-executable instructions thereupon for directing said capillary electrophoresis device to load and electrophoretically separate nucleic acid molecules in a nucleic acid sample, said instructions comprising:
      i) instructions to cause said device to immerse an end of a CE capillary into a nucleic acid sample; ii) instructions to cause said device to apply a voltage along said capillary for a time sufficient to introduce a plug of nucleic acid molecules from said sample into denaturing separation medium comprised by said capillary;
      iii) instructions to cause said device to move said end of said capillary to a separate reservoir;
      iv) instructions to cause said device to apply a voltage of reverse polarity to that applied in step (ii) along said capillary for a time and of a strength sufficient to expel nucleic acid material present at the tip of said capillary which has not entered said denaturing separation medium; and
      v) instructions to cause said device, after step (iv) to apply a voltage along said capillary in the direction applied in step (ii), to thereby electrophoretically separate nucleic acid molecules introduced to said separation medium.

24. The system of paragraph 23, wherein said instructions further comprise instructions for, after step (iv), and before step (v), transferring said end of said capillary to another reservoir comprising electrophoretic separation medium.

25. A method for reducing the relative magnitude of an artifact peak in denaturing nucleic acid capillary electrophoresis (CE), the method comprising:
   a) electrokinetically injecting a nucleic acid sample into one end of a CE capillary comprising a denaturing separation medium;
   b) transferring said end of said CE capillary to a reservoir of buffer substantially lacking nucleic acid sample, and transiently heating said capillary in an amount and for a time sufficient to cause expansion of said separation medium; and
   c) after step (b), electrophoretically separating said nucleic acid sample, wherein steps (a)-(c) reduce the magnitude of an artifact peak in the resulting separated species.

26. The method of paragraph 25, wherein said transient heating comprises joule heating of said capillary.

27. The method of paragraph 26, wherein said joule heating is achieved by application of a voltage in reverse polarity relative to voltage applied to electrokinetically inject said nucleic acid into said capillary.

28. The method of paragraph 25, wherein said expansion causes the expulsion of nucleic acid material present at the tip of said capillary which has not entered said denaturing separation medium.

29. The method of paragraph 25, wherein electrophoretic separating step (c) comprises transferring said end of said capillary to a second reservoir comprising electrophoresis buffer.

30. The method of paragraph 25, wherein said artifact peak comprises double-stranded DNA.

31. The method of paragraph 25, wherein said nucleic acid sample comprises a PCR reaction mixture.

32. The method of paragraph 25, wherein said nucleic acid sample substantially lacks formamide.

33. The method of paragraph 25, wherein said nucleic acid sample comprises formamide.

34. In a method for denaturing capillary electrophoretic separation of nucleic acids, the method comprising:
   a) immersing an end of a CE capillary comprising a denaturing separation medium in a sample comprising nucleic acid;
   b) applying a voltage along said CE capillary for a time and in a direction sufficient to introduce a plug of nucleic acids from said sample into said denaturing separation medium;
   c) transferring said end of said capillary to a reservoir comprising electrophoresis buffer and applying a voltage along said capillary to effect electrophoretic separation of nucleic acid species in said plug;
   the improvement comprising:
   after step (b) and before step (c), transferring said end of said capillary to a reservoir comprising a buffer substantially lacking nucleic acid; and
   heating at least said end of said capillary at temperature and for a duration sufficient to cause the expansion of said denaturing separation medium, whereby at least material present at the tip of said capillary which has not entered said denaturing separation medium is expelled from said end of said capillary, such that non-denatured nucleic acid from said sample substantially does not enter said separation medium in said capillary, whereby the magnitude of an artifact peak is reduced relative to the method performed without steps (i) and (ii).

35. The method of paragraph 34, wherein heating in step (ii) comprises joule heating of said capillary.

36. The method of paragraph 35, wherein said joule heating is effected by applying a voltage along said capillary in a reverse polarity relative to the voltage applied in steps (b) and (c).

37. The method of paragraph 34, wherein said artifact peak comprises double-stranded DNA.

38. The method of paragraph 34, wherein said nucleic acid sample comprises a PCR reaction mixture.

39. The method of paragraph 34, wherein said nucleic acid sample substantially lacks formamide.

40. The method of paragraph 34, wherein said nucleic acid sample comprises formamide.

41. A method for reducing relative magnitude of an artifact peak in denaturing nucleic acid capillary electrophoresis (CE), the method comprising:
   a) contacting an end of a CE capillary comprising a denaturing separation medium with a nucleic acid sample and applying a voltage along said capillary sufficient to introduce a plug of nucleic acids from said sample into the separation medium in said capillary;
   b) removing the end of said capillary from step (a) from said sample; and
   c) after step (b), applying heat to said capillary in an amount and for a time sufficient to cause expansion of the contents of said capillary, the expansion resulting in expulsion of material present at the tip of said capillary which has not entered said denaturing separation medium;
   whereby the magnitude of an artifact peak is reduced when nucleic acids in said plug are separated by electrophoretic separation of said sample through said capillary.

42. The method of paragraph 41, wherein step (c) comprises joule heating of said capillary.

43. The method of paragraph 42, wherein said joule heating is achieved by application of reverse-polarity voltage relative to the voltage applied to introduce said plug of nucleic acids into said capillary.

44. The method of paragraph 41, wherein said artifact peak comprises double-stranded DNA.

45. The method of paragraph 41, further comprising the step, after step (b) and before step (c) of immersing said end of said CE capillary in buffer substantially lacking nucleic acid sample.

46. The method of paragraph 41, further comprising, after step (c), the step of transferring said end of said capillary to a reservoir comprising electrophoretic separation buffer and electrophoretically separating nucleic acids in said plug.

47. The method of paragraph 41, wherein said nucleic acid sample comprises a PCR reaction mixture.

48. The method of paragraph 41, wherein said nucleic acid sample substantially lacks formamide.

49. The method of paragraph 41, wherein said nucleic acid sample comprises formamide.

50. A computer-readable, physical memory comprising computer-executable instructions thereupon for directing an automated capillary electrophoresis device to load and electrophoretically separate nucleic acid molecules in a nucleic acid sample, said instructions comprising:
   a) instructions to cause said device to immerse an end of a CE capillary into a nucleic acid sample;
   b) instructions to cause said device to apply a voltage along said capillary for a time sufficient to introduce a plug of nucleic acid molecules from said sample into separation medium comprised by said capillary;
   c) instructions to cause said device to move said end of said capillary to a separate reservoir;
   d) instructions to cause said device to apply a voltage of reverse polarity to that applied in step (b) along said capillary for a time and of a strength sufficient to expel material present at the tip of said capillary which has not entered said separation medium; and
   e) instructions to cause said device, after step (d) to apply a voltage along said capillary in the direction applied in step (b), to thereby electrophoretically separate nucleic acid molecules introduced to said separation medium.

51. The computer-readable medium of paragraph 50 wherein said instructions further comprise instructions for, after step (d), and before step (e), transferring said end of said capillary to another reservoir comprising electrophoretic separation medium.

52. A system for denaturing capillary electrophoresis, the system comprising
   a) a capillary electrophoresis device operatively linked to a computer processor;
   b) a computer-readable, physical memory comprising computer-executable instructions thereupon for directing said capillary electrophoresis device to load and electrophoretically separate nucleic acid molecules in a nucleic acid sample, said instructions comprising:
   i) instructions to cause said device to immerse an end of a CE capillary into a nucleic acid sample;
   ii) instructions to cause said device to apply a voltage along said capillary for a time sufficient to introduce a plug of nucleic acid molecules from said sample into separation medium comprised by said capillary;
   iii) instructions to cause said device to move said end of said capillary to a separate reservoir;
   iv) instructions to cause said device to apply a voltage of reverse polarity to that applied in step (ii) along said capillary for a time and of a strength sufficient to expel material present at the tip of said capillary which has not entered said separation medium; and
   v) instructions to cause said device, after step (iv) to apply a voltage along said capillary in the direction applied in step (ii), to thereby electrophoretically separate nucleic acid molecules introduced to said separation medium.

53. The system of paragraph 52, wherein said instructions further comprise instructions for, after step (iv), and before step (v), transferring said end of said capillary to another reservoir comprising electrophoretic separation medium.

It is understood that the foregoing detailed description and the following Examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example 1

Examination of the Nature of the Shadow Peaks

The nature of the shadow peaks was first examined by varying the temperature of at which the CE separation is performed after sample injection. Separation was performed at 27° C., 35° C., 45° C., and to 55° C. following injection at 95° C. FIG. 3 shows that shadow migration increased when separation was performed at 35° C. instead of 27° C., then decreased when separation was performed at 45° C., then increased again when separation was performed at 55° C. The break in migration shifts is indicative of a state transition of the shadow material.

The nature of the shadow peaks was further examined by varying the temperature at which sample was injected, with a single temperature used for separation. Injection was performed at 35° C., 55° C., 60° C. and 85° C. before separation at 35° C. At 35° C. and 55° C. there was only shadow peak observed. As shown in FIG. 4, there was a sharp transition between 55° C. and 60° C., at which point the main peak became apparent. Increasing the temperature of loading resulted in increased main peak magnitude. It was concluded that the main peak and the shadow peak have the same origin—with increasing temperature of injection, shadow peak is converted to main peak.

However, it was found that further increasing the temperature of injection from 85° C. to 95° C. did not appreciably change the main vs shadow proportion of the peaks (see FIG. 5). It was concluded that the main and shadow isoforms form during or after injection, and that the shadow isoform may undergo a state transition depending upon cartridge temperature. From the behavior noted in the preceding experiments, it was postulated that the main peak is single stranded DNA, while the shadow is double-stranded or partially double-stranded DNA that can melt depending upon gel temperature.

While not wishing to be bound by theory, FIGS. 6A-6H illustrate one series events postulated to give rise to shadow peaks. FIG. 6A illustrates the capillary prior to injection. At the start of injection (FIG. 6B), it is postulated that the CE gel heats up and expands as the injection current runs through it. The expansion extrudes a small amount of the gel into the sample. During the injection, denatured DNA electrokinetically flows into the capillary gel matrix (shown in large black dots FIG. 6C). After injection is complete, cooling of the capillary matrix permits it to contract. A plug of denatured DNA (single stranded, or ssDNA) has entered the denaturing separation medium, and the contraction of the gel in the capillary leaves a void at the tip of the capillary that is filled with sample solution. As it cools, ssDNA in the sample solution at the tip of the gel can re-nature to form dsDNA, shown in a brick pattern (FIGS. 6D and 6E). Urea denaturing agent in the gel prevents the re-naturation of ssDNA that has entered the gel, but as the tip of the capillary is moved from the sample to the buffer reservoir for separation, dsDNA forms in the liquid trapped in the void at the tip (FIG. 6E). ssDNA is in the gel, and dsDNA are present at the tip. FIGS. 6F and 6G show the situation postulated to occur as separation is performed. dsDNA enters the gel as separating voltage is applied. The urea in the gel, while sufficient to prevent renaturation of the ssDNA is not able to denature DNA that is double stranded when it enters the gel at ambient temperature. The dsDNA migrates faster, overtaking the ssDNA in the main peak to form a shadow peak. FIG. 6H shows events postulated to occur as the migrating DNA enters the heated cartridge body—depending upon the temperature of the cartridge, the dsDNA is postulated to either denature to ssDNA (brick pattern), which will form a split peak, or remain double-stranded, which will retain the shadow peak. Slower-migrating ssDNA (large black circles) remains single stranded throughout the separation.

An alternative, or possibly coincident series of injection-related events postulated to occur in the capillary and at the sample-loading capillary tip is shown in FIG. 7. The invention is not intended to be limited by theory; however, the following illustrates another proposed series of events contributing to shadow formation. FIG. 7 shows the capillary after injection—as the capillary cools following injection, there is ssDNA that has entered the denaturing separation medium (shown in small black dots) and DNA which has entered a zone of the gel at the interface in which the denaturing agent is diluted, and where re-naturation becomes possible (shown in horizontal stripes). Once the non-denatured DNA enters the gel, shadow and/or split peaks are possible as diagrammed in FIG. 6.

Example 2

Dismissing dsDNA from the Tip of the Capillary Before Separation Reduces Shadow Peak Artifacts Recognizing that shadow peaks may form when dsDNA forms at the tip of the capillary after injection, it was proposed and demonstrated herein that steps that dismiss the material at the tip of the capillary can reduce the incidence or the magnitude of the shadow artifact.

A brief reverse-polarity (RP) pulse was applied to the capillary after injection. This was compared to the application of a pulse in the same polarity as injection. FIGS. 8A-8D show the results of the application of no pulse, an RP pulse and a "normal" pulse on different single and multiplex amplification products. In FIG. 8A, a single-plex reaction is shown. The RP pulse clearly diminishes the relative magnitude of the shadow peak (red arrow) when compared to the non-pulsed run. The "normal" pulsed run did not show significant difference—without wishing to be bound by theory, it is thought that the "normal" pulse, even though performed while the tip is in a sample reservoir substantially lacking nucleic acid sample, serves only to push the re-natured DNA located at the tip of the capillary further into the capillary.

FIG. 8B shows the results of a similar experiment with a 3-plex PCR reaction product.

FIGS. 8C and 8D show the results of RP and "normal" pulsing relative to no pulse for two different hi-order multiplex amplification reactions. The RP pulse clearly reduces shadow formation.

In view of these results, application of a reverse-polarity pulse to the capillary after electrokinetic injection is useful to avoid shadow artifact peaks in denaturing capillary electrophoresis.

Example 3

Causing the Expansion of the CE Separation Matrix while the Loaded Tip is Immersed in Medium Substantially Lacking Nucleic Acid Sample Following Injection Another approach for dismissing the non-denatured DNA present at the tip of a loaded CE capillary is tested as follows. Following injection, the loaded tip is moved to a reservoir containing electrophoresis buffer (preferably, but not necessarily a separate reservoir form that used for separation). While the tip is immersed in that reservoir, a portion of the capillary, e.g., a portion of 2-20 cm, is heated, e.g., to 90° C. (alternatively heating to 85° C., 80° C., 75° C., 72° C., 70° C., 68° C., 66° C., 64° C., 62° C., 60° C. or less, but preferably at least 45° C.) for a time sufficient to cause expansion of matrix in the capillary. Temperature can be adjusted dependent upon the time the heat is applied. Generally, shorter times will be required for higher temperatures. Also, increasing the size of the portion of the capillary that is heated (e.g., from 10% of the capillary length, 20% of the capillary length, 30% of the capillary length, 40% of the capillary length, 50% of the capillary length, 60% of the capillary length, 70% of the capillary length, 80% of the capillary length, 90% of the capillary length or more, up to and including essentially the whole length of the capillary (e.g., when Joule heating is applied)), can decrease the time or heating temperature necessary to dismiss non-denatured DNA from the tip of the capillary. The time can be, e.g., about 3 to 30 seconds or more, and can be adjusted depending upon the temperature used. Following heating for the prescribed time (which can be determined with only routine experimentation for a given combination of temperature and time), the tip is either transferred to the separation reservoir for application of separating voltage, or separating voltage is applied directly, without the extra transfer.

Treating the capillary to cause the expansion of the capillary matrix while the loaded tip is immersed in medium substantially lacking nucleic acid sample can diminish shadow peak formation upon subsequent separation and detection.

The invention claimed is:

1. A method for reducing the magnitude of an artifact peak in denaturing nucleic acid capillary electrophoresis (CE), the method comprising:
   a) electrokinetically injecting a nucleic acid sample into one end of a CE capillary comprising a denaturing separation medium;
   b) applying a voltage of the opposite polarity to that used to inject said nucleic acid sample to said capillary, said voltage being of a strength and applied for a time sufficient to expel from said capillary nucleic acid which has not entered said denaturing separation medium;
   c) after step (b), electrophoretically separating nucleic acid in said capillary using a voltage in the same direction as that applied to electrokinetically inject said nucleic acid sample in step (a), wherein steps (a)-(c) reduce the magnitude of an artifact peak in the resulting separated species.

2. The method of claim 1, further comprising, before step (b), transferring said end of said capillary to a reservoir substantially lacking said nucleic acid sample.

3. The method of claim 1, wherein step (c) comprises, before said electrophoretically separating, transferring said end of said capillary to a separate reservoir comprising electrophoresis buffer.

4. The method of claim 1, wherein said artifact peaks comprise double-stranded DNA.

5. The method of claim 1, wherein said nucleic acid sample comprises a PCR reaction mixture.

6. The method of claim 1, wherein said nucleic acid sample substantially lacks formamide.

7. The method of claim 1, wherein said sample comprises formamide.

8. A computer-readable, physical memory comprising computer-executable instructions thereupon for directing an automated capillary electrophoresis device to load and electrophoretically separate nucleic acid molecules in a nucleic acid sample, said instructions comprising:
   a) instructions to cause said device to immerse an end of a CE capillary into a nucleic acid sample;
   b) instructions to cause said device to apply a voltage along said capillary for a time sufficient to introduce a plug of nucleic acid molecules from said sample into denaturing separation medium comprised by said capillary;
   c) instructions to cause said device to move said end of said capillary to a separate reservoir;
   d) instructions to cause said device to apply a voltage of reverse polarity to that applied in step (b) along said capillary for a time and of a strength sufficient to expel nucleic acid material present at the tip of said capillary which has not entered said denaturing separation medium; and
   e) instructions to cause said device, after step (d) to apply a voltage along said capillary in the direction applied in step (b), to thereby electrophoretically separate nucleic acid molecules introduced to said separation medium.

9. The computer-readable medium of claim 8, wherein said instructions further comprise instructions for, after step (d), and before step (e), transferring said end of said capillary to another reservoir comprising electrophoretic separation medium.

10. A system for denaturing capillary electrophoresis, the system comprising
   a) a capillary electrophoresis device operatively linked to a computer processor;
   b) a computer-readable, physical memory comprising computer-executable instructions thereupon for directing said capillary electrophoresis device to load and electrophoretically separate nucleic acid molecules in a nucleic acid sample, said instructions comprising:
      i) instructions to cause said device to immerse an end of a CE capillary into a nucleic acid sample;
      ii) instructions to cause said device to apply a voltage along said capillary for a time sufficient to introduce a plug of nucleic acid molecules from said sample into denaturing separation medium comprised by said capillary;
      iii) instructions to cause said device to move said end of said capillary to a separate reservoir;
      iv) instructions to cause said device to apply a voltage of reverse polarity to that applied in step (ii) along said capillary for a time and of a strength sufficient to expel nucleic acid material present at the tip of said capillary which has not entered said denaturing separation medium; and
      v) instructions to cause said device, after step (iv) to apply a voltage along said capillary in the direction applied in step (ii), to thereby electrophoretically separate nucleic acid molecules introduced to said separation medium.

11. The system of claim 10, wherein said instructions further comprise instructions for, after step (iv), and before step (v), transferring said end of said capillary to another reservoir comprising electrophoretic separation medium.

12. A method for reducing the relative magnitude of an artifact peak in denaturing nucleic acid capillary electrophoresis (CE), the method comprising:
   a) electrokinetically injecting a nucleic acid sample into one end of a CE capillary comprising a denaturing separation medium;
   b) transferring said end of said CE capillary to a reservoir of buffer substantially lacking nucleic acid sample, and transiently heating said capillary in an amount and for a time sufficient to cause expansion of said separation medium; and
   c) after step (b), electrophoretically separating said nucleic acid sample, wherein steps (a)-(c) reduce the magnitude of an artifact peak in the resulting separated species.

13. The method of claim 12, wherein said transient heating comprises joule heating of said capillary.

14. The method of claim 13, wherein said joule heating is achieved by application of a voltage in reverse polarity relative to voltage applied to electrokinetically inject said nucleic acid into said capillary.

15. The method of claim 12, wherein said expansion causes the expulsion of nucleic acid material present at the tip of said capillary which has not entered said denaturing separation medium.

16. The method of claim 12, wherein electrophoretic separating step (c) comprises transferring said end of said capillary to a second reservoir comprising electrophoresis buffer.

17. The method of claim 12, wherein said artifact peak comprises double-stranded DNA.

18. The method of claim 12, wherein said nucleic acid sample comprises a PCR reaction mixture.

19. The method of claim 12, wherein said nucleic acid sample substantially lacks formamide.

20. The method of claim 12, wherein said nucleic acid sample comprises formamide.

* * * * *